United States Patent
Von Kalle et al.

(10) Patent No.: US 9,493,827 B2
(45) Date of Patent: Nov. 15, 2016

(54) DETERMINATION OF IN VIVO DNA DOUBLE-STRAND BREAK LOCALIZATION AND APPLICATION THEREOF

(75) Inventors: Christof Von Kalle, Freiburg (DE); Manfred Schmidt, St. Leon-Rot (DE); Richard Gabriel, Schriesheim (DE); Ali Nowrouzi, Heidelberg (DE); Anne Arens, Schwetzingen (DE); Angelo Lombardo, Milan (IT); Luigi Naldini, Milan (IT)

(73) Assignees: Deutsches Krebsforschungszentrum, Heidelberg (DE); Ospedale San Raffaele SRL, Milan (IT)

( * ) Notice: Subject to any disclaimer, the term of this patent is extended or adjusted under 35 U.S.C. 154(b) by 0 days.

(21) Appl. No.: 13/522,225

(22) PCT Filed: Jan. 13, 2011

(86) PCT No.: PCT/EP2011/050380
§ 371 (c)(1),
(2), (4) Date: Sep. 7, 2012

(87) PCT Pub. No.: WO2011/086118
PCT Pub. Date: Jul. 21, 2011

(65) Prior Publication Data
US 2013/0143204 A1    Jun. 6, 2013

Related U.S. Application Data

(60) Provisional application No. 61/295,135, filed on Jan. 14, 2010.

(51) Int. Cl.
*C12Q 1/68* (2006.01)
*C12Q 1/70* (2006.01)
*C12N 15/90* (2006.01)

(52) U.S. Cl.
CPC ............ *C12Q 1/686* (2013.01); *C12N 15/907* (2013.01); *C12Q 1/6827* (2013.01); *C12Q 1/6858* (2013.01); *C12Q 1/70* (2013.01); *C12N 2740/15021* (2013.01); *C12N 2740/15031* (2013.01); *C12N 2740/15045* (2013.01)

(58) Field of Classification Search
None
See application file for complete search history.

(56) References Cited

U.S. PATENT DOCUMENTS

| | | | |
|---|---|---|---|
| 6,514,706 B1 * | 2/2003 | Von Kalle et al. | 435/6.12 |
| 2007/0134796 A1 * | 6/2007 | Holmes et al. | 435/455 |
| 2008/0131962 A1 * | 6/2008 | Miller | 435/325 |
| 2008/0159996 A1 * | 7/2008 | Ando et al. | 424/93.21 |
| 2009/0111119 A1 * | 4/2009 | Doyon et al. | 435/6 |

FOREIGN PATENT DOCUMENTS

WO    WO 00/24929    5/2000

OTHER PUBLICATIONS

Gabriel Richard et al: "A Novel Method for Analyzing Zinc Finger Nuclease Specificity In Vivo by LAM-PCR of Integrase Defective Lentiviral Vector (IDLV) Captured by DNA Double-Strand Breaks (DSB)", Molecular Therapy, vol. 17, No. Suppl. 1 ,May 2009, p. S284, from 12th Annual Meeting of the American Society of Gene Therapy; San Diego, CA.*
Lombardo Angelo et al: "Gene editing in human stem cells using zinc finger nucleases and integrase-defective lentiviral vector delivery.", Nature Biotechnology, Nov. 2007 LNKD-PUBMED:1 7965707, vol. 25, No. 11 ,Nov. 2007, pp. 1298-1306.*
Lombardo et al. (Gene editing in human stem cells using zinc finger nucleases and integrase-defective lentiviral vector delivery, Nature Biotechnology, vol. 25, No. 11, Nov. 2007.*
Urnov et al. (Highly efficient endogenous human gene correction using designed zinc-finger nucleases, Nature, vol. 435, No. 2, Jun. 2005)).*
Schnepp et al. (Characterization of Adeno-Associated Virus Genomes Isolated from Human Tissues, Journal of Virology, Dec. 2005, p. 14793-14803).*
Schmidt et al. (High-resolution insertion-site analysis by linear amplification-mediated PCR (LAM-PCR), Nature Methods, vol. 4, No. 12, p. 1051-1057, Dec. 2007).*
Gabriel et al. (Comprehensive genomic access to vector integration in clinical gene therapy, Nature Medicine, vol. 15, No. 12, p. 1431-1437, Nov. 22, 2009).*
Gabriel et al. (hereinafter "Gabriel2"; A Novel Method for Analyzing Zinc Finger Nuclease Specifi city In Vivo by LAM-PCR of Integrase Defective Lentiviral Vector (IDLV) Captured by DNA Double-Strand Breaks (DSB), Molecular Therapy vol. 17, Supplement 1, May 2009).*
Wang et al. (DNA bar coding and pyrosequencing to analyze adverse events in therapeutic gene transfer, Nucleic Acids Research, 2008, vol. 36, No. 9, Apr. 14, 2008).*
Harkey et al. (Multiarm High-Throughput Integration Site Detection: Limitations of LAM-PCR Technology and Optimization for Clonal Analysis, Stem Cells and Development 16:381-392 (2007)).*
Meuller et al. (In Vivo Footprinting of a Muscle Specific Enhancer by Ligation Mediated PCR, Science, vol. 246, pp. 780-786, Nov. 10, 1989).*
Silver et al. (Novel Use of Polymerase Chain Reaction to Amplify Cellular DNA Adjacent to an Integrated Provirus, Journal of Virology, vol. 63, No. 5, May 1989, p. 1924-1928).*

(Continued)

*Primary Examiner* — Aaron Priest
(74) *Attorney, Agent, or Firm* — Foley & Lardner LLP

(57) ABSTRACT

The present invention relates to a method for determining the in vivo localization of double-strand breaks in a host cell, comprising incubating a host cell suspected to comprise DNA double-strand breaks and a linear polynucleotide comprising a known sequence, detecting the in vivo insertion sites of said polynucleotide in the genome of said host cell, and assessing the in vivo localization of double-strand breaks. Further envisaged by the present invention is a method for obtaining an endonuclease with altered in vivo specificity. Finally, the present invention is directed to a kit for determining in vivo specificity of an endonuclease.

15 Claims, 8 Drawing Sheets

(56) References Cited

OTHER PUBLICATIONS

Figure 2A:
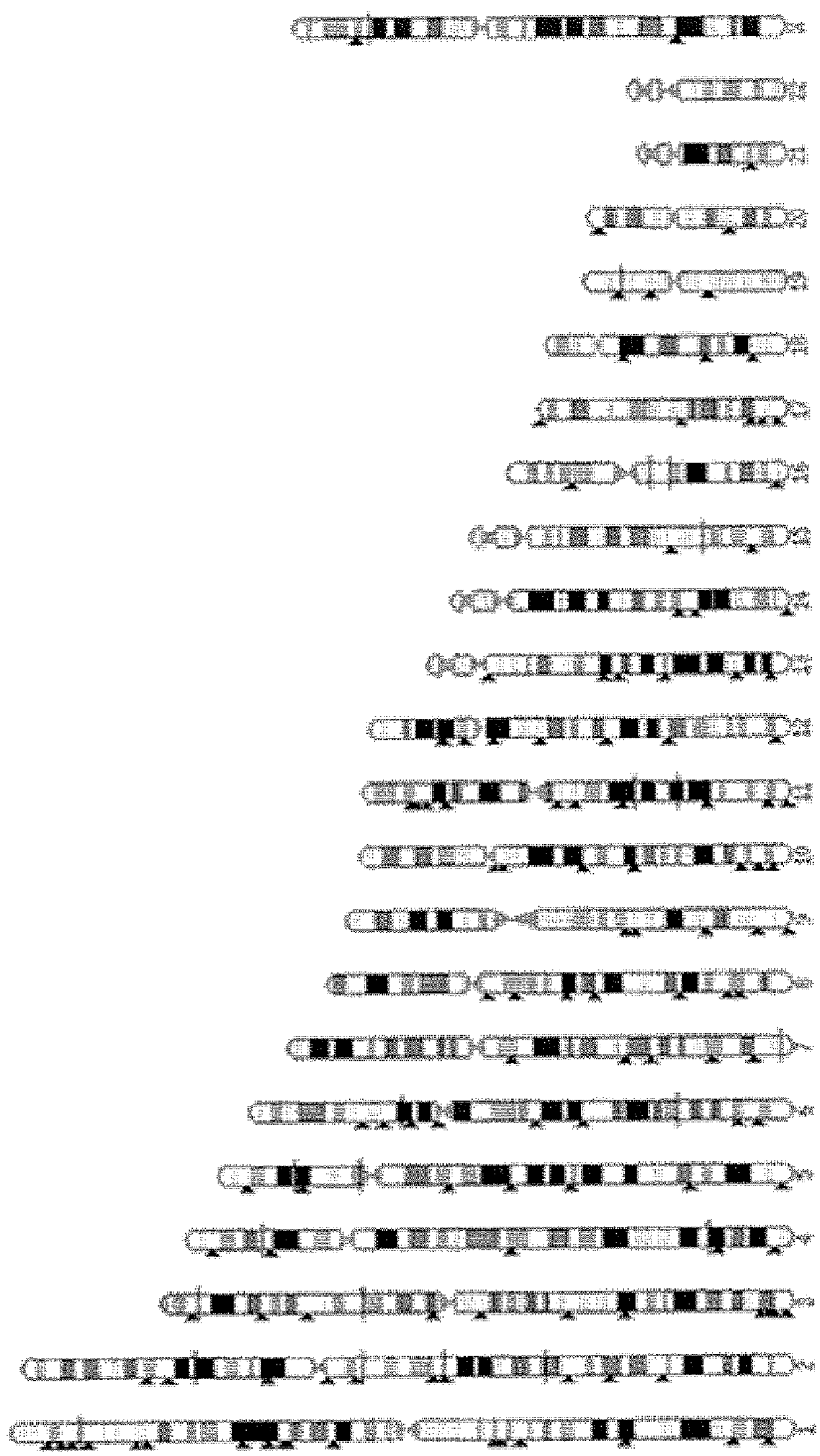

Vargas et al. (Novel Integrase-Defective Lentiviral Episomal Vectors for Gene Transfer, Human Gene Therapy 15:361-372 (Apr. 2004).*
Philippe et al. (Lentiviral vectors with a defective integrase allow efficient and sustained transgene expression in vitro and in vivo, PNAS, vol. 103, No. 47, pp. 17684-17689, Nov. 21, 2006).*
Miller et al. (Adeno-associated virus vectors integrate at chromosome breakage sites, Nature Genetics, vol. 36 | No. 7 | Jul. 2004).*
Meng et al. (Targeted gene inactivation in zebrafish using engineered zinc-finger nucleases, Nat Biotechnol. Jun. 2008;26(6):695-701).*
Hockemeyer et al. (Efficient targeting of expressed and silent genes in human ESCs and iPSCs using zinc-finger nucleases, Nature Biotechnology 27, 851-857, Published online Aug. 13, 2009).*
Perez et al. (Establishment of HIV-1 resistance in CD4+ T cells by genome editing using zinc-finger nucleases, Nature Biotechnology 26, 808-816, Published online Jun. 29, 2008).*
Doyon et al. (Heritable targeted gene disruption in zebrafish using designed zinc-finger nucleases, Nature Biotechnology 26, 702-708 (2008)).*
Santiago et al. (Targeted gene knockout in mammalian cells by using engineered zinc-finger nucleases, PNAS, Apr. 15, 2008 vol. 105 No. 15).*
Klug et al. (The Discovery of Zinc Fingers and Their Applications in Gene Regulation and Genome Manipulation, Annu. Rev. Biochem. 2010. 79:213-31).*
Miller et al. (Adeno-associated virus vectors integrate at chromosome breakage sites, Nat Genet. Jul. 2004;36(7):767-73. Epub Jun. 20, 2004).*
Haviv-Chesner et al. (Capture of linear fragments at a double-strand break in yeast, Nucleic Acids Res. 2007;35(15):5192-202. Epub Aug. 1, 2007).*
Gabriel et al. (A Novel Method for Analyzing Zinc Finger Nuclease Specificity In Vivo by LAM-PCR of Integrase Defective Lentiviral Vector (IDLV) Captured by DNA Double-Strand Breaks (DSB), Molecular Therapy vol. 17, Supplement 1, May 1, 2009).*
Iiizumi et al. (Impact of non-homologous end-joining deficiency on random and targeted DNA integration: implications for gene targeting, Nucleic Acids Res. Nov. 2008;36(19):6333-42. Epub Oct. 3, 2008).*
Ledford et al. (Gene-therapy enzymes make unpredicted errors, Nature, doi:10.1038/news.2011.461, Published online Aug. 7, 2011).*
Gabriel et al., An unbiased genome-wide analysis of zinc-finger nuclease specificity, Nat Biotechnol. Aug. 7, 2011;29(9):816-23. doi: 10.1038/nbt.1948.*
Altschul, et al., "Basic Local Alignment Search Tool," *J Mol Biol* 215(3), pp. 403-410 (1990).
Lombardo, et al., "Gene editing in human stem cells using zinc finger nucleases and integrase-defective lentiviral vector delivery," *Nat Biotechnol* 25(11): pp. 1298-1306 (2007).
Porteus, et al., Efficient Gene Targeting Mediated by Adeno-Associated Virus and DNA Double-Strand Breaks, *Nat Biotechnol* 23(8): pp. 967-73 (2005).
Banasik, et al., "Integrase-defective lentiviral vectors: progress and applications," *Gene Therapy*, vol. 17, No. 2, pp. 150-157 (2009).
Durai, et al., "Zinc finger nucleases: custom-designed molecular scissors for genome engineering of plant and mammalian cells," *Nucleic Acids Research* 2005, vol. 33, No. 18, pp. 5978-5990 (2005).
Schmidt, et al., "High-resolution insertion-site analysis by linear amplification-mediated PCR" *Nature Methods*, vol. 4, No. 12, pp. 1051-1057 (2007).
Gabriel, et al., "Comprehensive genomic access to vector integration in clinical gene therapy" *Nature Medicine*, vol. 15, No. 12, pp. 1431-1436 (2009).
Gabriel, et al., "A novel method for analyzing zinc finger nuclease . . . " Molecular Therapy, vol. 17, No. Suppl. 1, p. S284 (2009).

Szczepek, et al., "Structure-based redesign of the dimerization interface reduces the toxicity of zinc-finger nucleases," *Nat Biotechnol* 25(7), pp. 786-793 (2007).
Porteus, et al., "Efficient gene targeting mediated by adeno-associated virus and DNA double-strand breaks", *Molecular and Cellular Biology*, vol. 23, No. 10, pp. 3558-3565 (2001).
Howe, et al., "Insertional mutagenesis combined with acquired somatic mutations causes leukemogenesis following gene therapy of SCID-X1 patients," *J Clin Invest* 118(9): 3143-50 (2008). Also encludes Supplemental Sheets and Tables.
Honma, et al., "Deletion, Rearrangement, and Gene Conversion; Genetic Consequences of Chromosomal Double-Strand Breaks in Human Cells," *Environ Mol Mutagen* 42(4), pp. 288-298 (2003).
Honma, et al., "Non-homologous end-joining for repairing I-SceI-induced DNA double strand breaks in human cells," *DNA Repair (Amst)* 6(6), pp. 781-788 (2007).
Cathomen, et al., "Zinc-finger Nucleases: The Next Generation Emerges," *Mol Ther* 16(7), pp. 1200-1207 (2008).
Durai S., et al., "Zinc finger nucleases: custom-designed molecular scissors for genome engineering of plant and mammalian cells," *Nucleic Acids Res* 33(18), pp. 5978-5990 (2005).
Gaur, et al., "Mutations in the Human Immunodeficiency Virus Type 1 Integrase D,D(35)E Motif Do not Eliminate Provirus Formation," *J Virol* 72(6), pp. 4678-4685 (1998).
Gotoh, "An Improved Algorithm for Matching Biological Sequences," *J Mol Biol* 162(3): 705-8 (1982).
Hacein-Bey-Abina, et al., "Insertional oncogenesis in 4 patients after retrovirus-mediated gene thereapy of SCID-X1," *J Clin Invest* 118(9): 3132-3142 (2008).
Hacein-Bey-Abina, et al., "A Serious Adverse Event after Successful Gene Therapy for X-Limited Severe Combined Immunodeficiency," *N Engl J Med* 348(3), pp. 255-266 (2003).
Kent, "The Blast-Like Alignment Tool," *Genome Res* 12(4), pp. 656-664 (2002).
Kim, et al., "Hybrid restriction enzymes: Zinc finger fusions to Fok 1 cleavage domain," *Proc Natl Acad Sci USA* 93(3), pp. 1156-1160 (1996).
Li, et al., "Role of the non-homologous DNA end joining pathway in the early steps of retroviral infection," *EMBO J* 20(12), pp. 3272-3281 (2001).
Lombardo, et al., "Gene editing in human stem cells using zinc finger nucleases and integrase-defective levtiviral vector delivery" vol. 25, No. 11, pp. 1298-1306 (2007).
Mani, et al., "Binding of two Zinc finger nuclease monomers to two specific sites is required for effective double-strand DNA cleavage," *Biochem Biophys Res Commun* 334(4): 1191-7 (2005).
Miller, et al., "Adeno-associated virus vectors integrate at chromosome breakage sites," *Nat Genet* 36(7): 767-73 (2004).
Miller, et al., "An improved zinc-finger nuclease architecture for highly specific genome editing," *Nat Biotechnol* 25(7): 778-85 (2007).
Modlich, et al., Cell-culture assays reveal the importance of retroviral vector design for insertional genotoxicity, *Blood* 108(8): 2545-53 (2006).
Montini, et al., "Hematopoietic stem cell gene transfer in a tumor-prone mouse model uncovers low genotoxicity of lentiviral vector integration," *Nat Biotechnol* 24(6): 687-96 (2006).
Nightingale, et al., "Transient Gene Expression by Nonintegrating Lentiviral Vectors," *Mol Ther* 13(6), pp. 1121-1132 (2006).
Ott, M.G., M. Schmidt, et al. (2006), Nat Med 12(4): 401-9.
Perez, et al., "Establishment of HIV-1 Resistance in CD4+ T cells by genome editing using zinc-finger nucleases," *Nat Biotechnol* 26(7): 808-16 (2008).
Smith, "Identification of Common Molecular Subsequences," *J Mol Biol* 147(1): 195-197 (1981).
International Preliminary Report on Patentability issued in related International Patent Application No. PCT/EP2011/050380, dated Jul. 26, 2012.

* cited by examiner

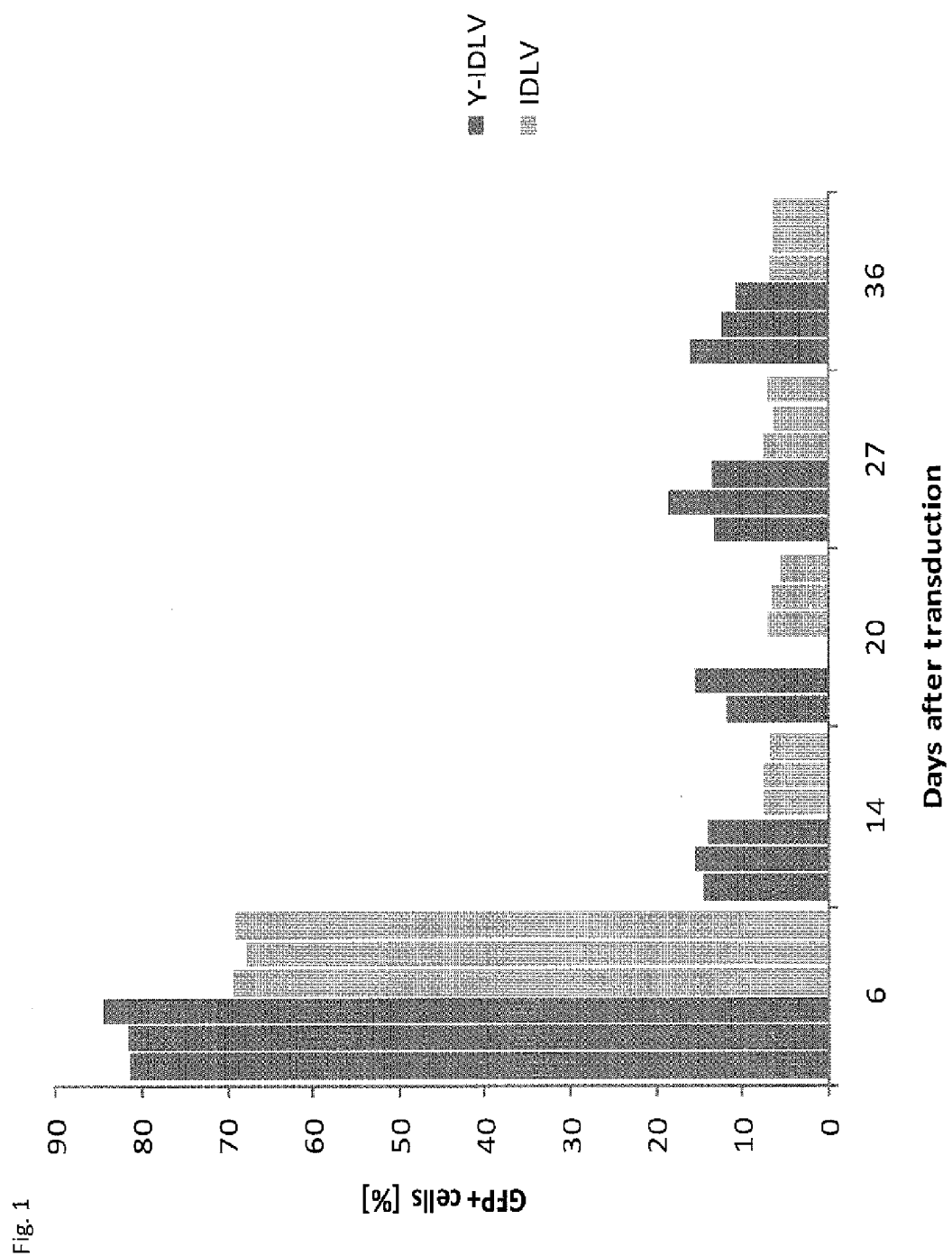

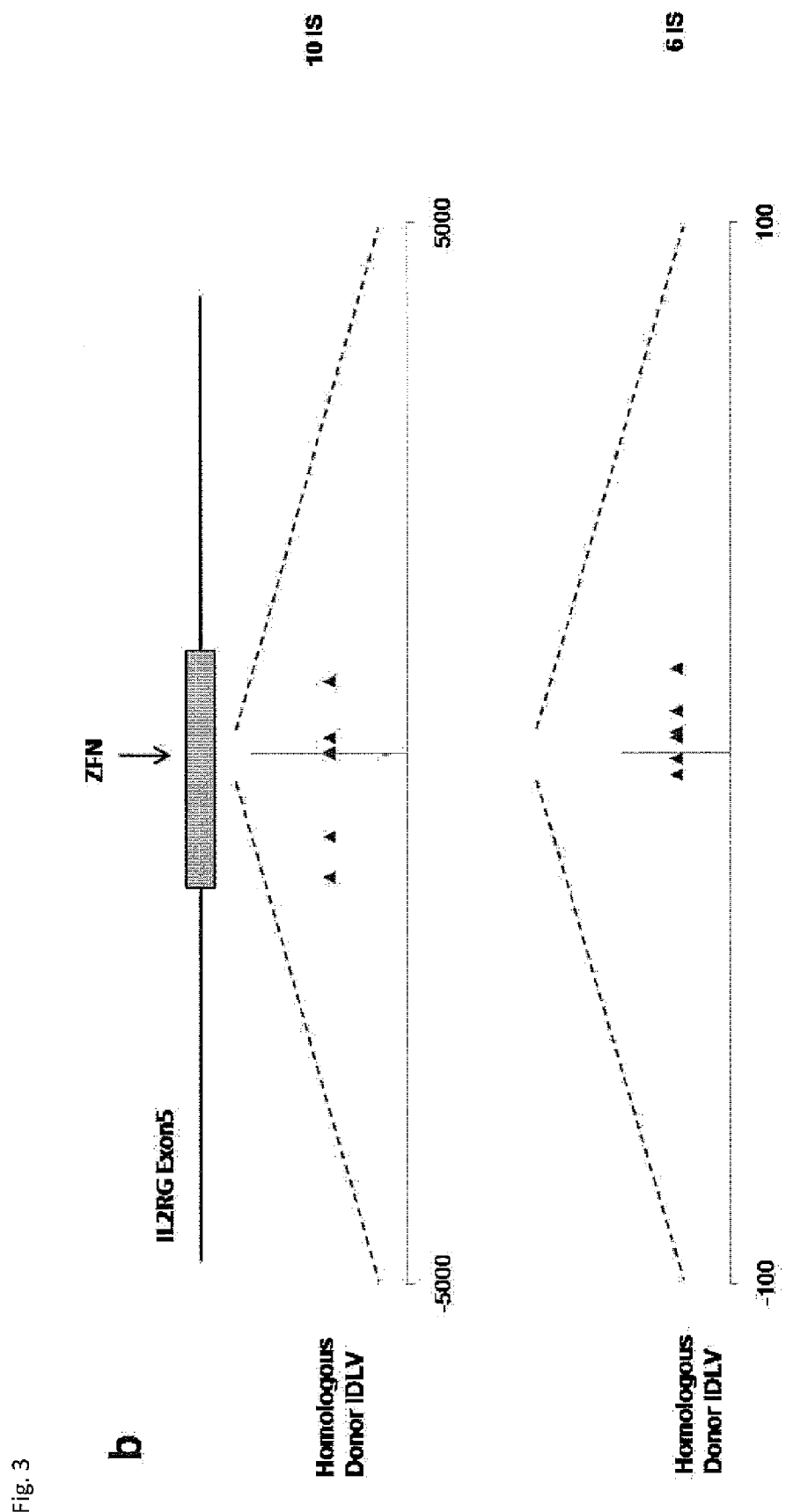

Fig. 5

ZFN-L (7)

GTCATCCCTCATC

ZFN-R (15)

AAACTGCAAAAG

DETERMINATION OF IN VIVO DNA DOUBLE-STRAND BREAK LOCALIZATION AND APPLICATION THEREOF

SEQUENCE LISTING

The instant application contains a Sequence Listing which has been submitted in ASCII format via EFS-Web and is herein incorporated by reference in its entirety.

The DNA repair machinery of live cells will seek to repair double strand breaks (DSBs) by homologous recombination (HR) ad integrum or by the more error-prone non-homologous end joining (NHEJ) pathway that essentially religates whatever sequence is available to the open remaining DNA strands. Spontaneous HR is a very rare event in mammalian cells with approximately 1 donor DNA recombination per $10^6$ cells (Cathomen and Joung 2008). This rate increases drastically when cells are exposed to agents that induce DSBs, like e.g. ionizing radiation; also, introduction of DSB by ZFN has been shown to potentiate the likelihood of HR at the cleavage site by a factor of 100-10000 (Durai et al. 2005; Porteus and Carroll 2005), making artificial ZFN a promising tool for genetic manipulation of live cells, including clinical therapy. DSB get repaired quickly, leaving no or only minor nucleotide changes or deletions in the genome, so it has been difficult to obtain data relating to the localization and/or frequency of double-strand breaks occurring in the genome of a cell.

Zinc finger nucleases (ZFNs) are artificial restriction enzymes comprising a zinc finger DNA-binding domain fused to a DNA-cleavage domain. ZFNs are designed to introduce DSBs at virtually any selected genome position. To achieve site-specific genome targeting, ZFNs combine unspecific Fok I endonuclease cleavage domains with arbitrary chosen binding domains of zinc finger proteins (ZFPs). Thereby, ZFN function requires the dimerization of a specific ZFN monomer binding upstream to the target site on the plus strand with a second ZFN-monomer that binds downstream of the target site (Kim et al. 1996; Mani et al. 2005). To reduce cytotoxicity of ZFN, mainly caused by homodimer formation of identical ZFN monomers at off-target sites, a new generation of ZFN has been developed by introducing complementary substitutions of single amino acids in the nuclease domain preventing homodimerization of the Fokl subunits (Miller et al. 2007; Szczepek et al. 2007).

Therapeutic applications of ZFN comprise three main categories of DNA modifications in live cells: i) targeted mutagenesis (gene knock-out), inducing loss of information during NHEJ, ii) gene correction at the target locus by HR involving a homologous donor DNA fragment and iii) targeted integration of an expression cassette by HR into a potentially "safe harbor" sequence whose mutation should be harmless for the targeted cell type. The mode of transfer of ZFN into cells is highly relevant for the success rate and toxicity of specific DNA modification in live cells. It was previously demonstrated that the delivery of ZFN into cells via non-integrating integrase-defective lentiviral vectors (IDLV) has little or no acute cytotoxicity, achieves transfer of the ZFN cDNA into almost every target cell, and has the potential to achieve HR mediated editing of the genome sequence specifically in up to 50% of the transduced cell populations (Lombardo et al. 2007). However, because DSB get repaired quickly, leaving no or only minor nucleotide changes or deletions in the genome, no definitive data has been available neither on the nature nor on the frequency of "off-site" DSB caused by ZFN activity outside of the intended target sequence. This remains an important open issue in using ZFN technology, not least if its application is intended for clinical gene therapy, since the availability of specific genomic editing would minimize or abolish the risk of insertional mutagenesis and oncogenesis observed in preclinical studies and clinical trials with retroviral vectors (Hacein-Bey-Abina et al. 2003; Modlich et al. 2006; Montini et al. 2006; Ott et al. 2006; Hacein-Bey-Abina et al. 2008; Howe et al. 2008).

Thus, means and methods are required for complying with the aforementioned needs. The said technical problem is solved by the embodiments characterized in the claims and herein below.

Accordingly, the present invention relates to a method for determining the in vivo localization of double-strand breaks in a host cell, comprising a) incubating said host cell suspected to comprise DNA double-strand breaks and a linear polynucleotide comprising a known sequence, b) detecting the in vivo insertion sites of said polynucleotide in the genome of said host cell, c) determining the in vivo positions of double-strand breaks, and d) assessing the in vivo localization of double-strand breaks.

The term "DNA double-strand break" or "double-strand break" is understood by the skilled artisan.

The term "determining the in vivo localization of double-strand breaks", preferably, relates to determining the positions in the genome of a host cell of double-strand breaks occurring in said host cell. It is to be understood that determining the localization of double-strand breaks according to the current specification includes the repair of said double-strand breaks, i.e. the double-strand breaks do no longer exist by the times their position is determined. It is further to be understood that the determination of the in vivo localization of double-strand breaks does not determine the exact position in the genome where the double-strand break occurred. However, the term requires that the position determined is within 10, 25, 50, 100, 250, 500, 1000, 2500, or 5000 nucleotides from the position where the double-strand break occurred for at least 75%, 85%, 90%, 95%, 97%, or 99% of the double-strand breaks examined.

As used herein, the term "incubating" relates to maintaining host cells under controlled conditions favorable for maintenance and/or growth of said host cells, preferably in an incubator. It is, however, also contemplated by the current invention that the host cells are comprised in a tissue or an organism.

The term "host cell" relates to a cell comprising the components required for at least one of the DNA repair systems mediating double strand break repair by homologous recombination ad integrum (HR) or by non-homologous end joining (NHEJ). Preferably, the host cell is a eukaryotic cell, more preferably a mammalian cell, even more preferably a human cell, and most preferably the host cell is a K562 cell. Preferably, the host cell is a cell originating from an organism whose genome has been completely sequenced.

The terms "linear polynucleotide comprising a known sequence" or "linear polynucleotide", preferably, relate to a polynucleotide comprising at least one stretch of nucleotides with a known nucleotide sequence. Preferably, said stretch is at least 18, at least 19, at least 20, at least 25, or at least 50 nucleotides long. Preferably, the nucleotide sequence of the linear polynucleotide is known in its entirety.

It is also contemplated by the current invention that the linear polynucleotide comprises additional sequences. Preferably, said additional sequences code for an integrase-deficient lentivirus, comprising, preferably, an expressible gene for a selectable marker, like, e.g. hygromycin phosphotransferase (Hygromycin B kinase, EC 2.7.1.119) or neomycin-kanamycin phosphotransferase (Kanamycin kinase, EC 2.7.1.95). Preferably, the endonuclease is comprised in said linear polynucleotide in an expressible form.

As used herein, the term "in vivo insertion sites", preferably, relates to the positions in the genome of a host cell wherein copies of the linear polynucleotide are covalently integrated by means of the cellular HR or the NHEJ systems. It is to be understood that not every DSB induced by an endonuclease and repaired by cellular systems in the presence of a linear polynucleotide will lead to the covalent integration of said linear polynucleotide. However, the term requires that in a given population of host cells used for the determination according to this specification, the number of insertion events is high enough to permit a statistical analysis of the insertion sites. Preferably, at least 50, at least 75, at least 85, at least 90, at least 100, or at least 250 insertion events are analyzed.

The term "in vivo positions of double-strand breaks", preferably relates to positions in the genome of a host cell where at least one double-strand break occurred.

As used herein, the term "determining the in vivo positions of double-strand breaks" relates to establishing the positions in the genome of a host cell where at least one double-strand break occurred. Preferably, determining the in vivo positions of double-strand breaks comprises the following steps: i) amplifying genomic regions comprising insertion sites. Preferably, amplification is achieved by PCR, more preferably by Linear Amplification Mediated PCR (LAM-PCR, WO/2000/024929), using the information on the known nucleotide sequence comprised in the linear polynucleotide to design specific primers for PCR amplification; ii) Sequencing the amplified polynucleotides obtained in step i); and iii) allocating insertion sites to positions of double-strand breaks.

As used in the current specification, the term "endonuclease" relates to an enzyme hydrolysing phosphodiester bonds within a polynucleotide. Preferably, both strands of DNA are hydrolysed. More preferably, the hydrolysis sites of opposing strands are separated by not more than 100, 50, 25, 20, 15, 10 nucleotides, such that one of the cellular DSB repair systems acts on the ends generated by said hydrolysis. Preferably, the hydrolysis sites are located at a distance of not more than 50, 100, 250, 500, 1000, 2000, 5000, or 10000 nucleotides from the recognition site of the endonuclease. More preferably, the endonuclease is a homing endonuclease or a type I restriction endonuclease. Most preferably, the endonuclease is a Zinc finger endonuclease (ZFN), comprising an endonuclease domain, e.g. the non-specific DNA cleavage domain of the FokI restriction endonuclease (Kim et al. 1996; Mani et al. 2005), and a DNA binding domain comprising at least one, at least two, or at least three zinc finger domains.

The definitions made above apply mutatis mutandis to the following:

In a further preferred embodiment, the current invention relates to a method for determining the in vivo specificity of an endonuclease, comprising a) incubating a host cell comprising said endonuclease and a linear polynucleotide comprising a known sequence, b) detecting the in vivo insertion sites of said polynucleotide in the genome of said host cell, c) determining the in vivo recognition sites of said endonuclease, and d) assessing the in vivo specificity of said endonuclease.

The term "determining the in vivo specificity" relates to determining the relative number of recognition sites 100% identical with the known recognition site of an endonuclease leading to the insertion of a linear polynucleotide as compared to the total number of insertion sites determined. It is, however, also contemplated by the current specification that for each recognition site identified the similarity to the known recognition site of the endonuclease is determined, so that a consensus sequence can be calculated. A person skilled in the art knows how to obtain an endonuclease with a known recognition site. This is e.g. accomplished by testing the hydrolytic activity of an endonuclease in the presence of various oligo- and/or polynucleotides. Also, e.g. an endonuclease with a known recognition site can be selected, e.g. by phage display. It is, however, also contemplated by the current invention that the known recognition site is e.g. generated by modularly assembling zinc-finger domains of known specificity.

The term "recognition site" relates to sequences in the genome of a host cell bound by the endonuclease of the current specification. Preferably, the binding of a ZFN is mediated by the at least on zinc finger domain interacting with the nucleotides of the recognition site.

As used herein, the term "determining the in vivo recognition sites" relates to establishing the recognition sites bound in vivo by the endonuclease of the current specification. Preferably, determining the in vivo recognition sites comprises the following steps: i) amplifying genomic regions comprising insertion sites. Preferably, amplification is achieved by PCR, more preferably by Linear Amplification Mediated PCR (LAM-PCR, WO/2000/024929 which is herewith incorporated by reference with respect to its entire disclosure content), using the information on the known nucleotide sequence comprised in the linear polynucleotide to design specific primers for PCR amplification; ii) Sequencing the amplified polynucleotides obtained in step i); and iii) allocating insertion sites to recognition sites. Preferably, allocation is achieved by bioinformatic methods, comprising identifying sequences comprising the linear polynucleotide of the current invention, determining genomic sequences adjacent to said linear polynuceotide, aligning said genomic sequences to the genome of the host cell, in silico prediction of potential endonuclease binding sites, and identifying potential binding sites in physical proximity to insertion sites.

In a further preferred embodiment, the current invention relates to a method for obtaining an endonuclease with an altered in vivo specificity, comprising a) providing at least one mutant of an endonuclease with a known recognition sequence, b) determining the in vivo specificity of said mutant of an endonuclease by the method of any one of claims 9 to 13, c) comparing the recognition sites recognized by said at least one mutant endonuclease with the recognition sites recognized by the unmodified endonuclease, and d) obtaining an endonuclease with an altered in vivo specificity.

As used in this specification, the term "altered in vivo specificity", preferably, relates to an in vivo specificity which is different from the in vivo specificity of an unmodified second endonuclease used for comparison. The alteration is an increase or decrease in the relative number of recognition sites 100% identical with the theoretical recognition site of an endonuclease; e.g. the relative number of recognition sites 100% identical with the theoretical recognition site is increased by at least 5%, 10%, 15%, 25%, or 50%. It is, however, also contemplated that the alteration is a change in the consensus sequence determined by the method of the current invention as described above.

A "mutant of an endonuclease" or "mutant endonuclease" as used herein relates to an endonuclease molecule comprising at least one amino acid exchange and/or at least one insertion and/or at least one deletion of at least one amino acid as compared to the unmodified endonuclease, wherein said mutant endonuclease still has the activity of hydrolyzing DNA. Preferably, said mutant endonuclease is obtained by mutagenizing an expressible gene of an endonuclease with a known recognition site.

As used herein, the term "providing at least one mutant of an endonuclease" relates to making available at least one mutant endonuclease in a host cell. Preferably, said at least one mutant endonuclease is made available by expressing a mutagenized gene for an endonuclease in said host cell.

"Comparing the recognition sites" as used herein relates to comparing the in vivo specificity determined for the mutant endonuclease with the in vivo specificity determined for the unmodified endonuclease. Preferably, the altered in vivo specificity is an increased in vivo specificity, meaning an in vivo specificity wherein an increased relative number of recognition sites is 100% identical with the known recognition site. It is, however, also contemplated by the current specification that an increased in vivo specificity means that the consensus sequence determined by the method of the current invention as described above comprises a lower frequency of alternative nucleotides in at feast one position of the consensus sequence.

In a further preferred embodiment, the current invention relates to a kit for determining the in vivo specificity of an endonuclease, comprising a polynucleotide providing a linear form in a host cell and a manual.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the said methods. The instructions can be provided by a user's manual in paper- or electronic form. For example, the manual may comprise instructions for interpreting the results obtained when carrying out the aforementioned methods using the kit of the present invention.

LITERATURE

Altschul, S. F., W. Gish, et al. (1990). "Basic local alignment search tool." *J Mol Biol* 215(3): 403-10.
Cathomen, T. and J. K. Joung (2008). "Zinc-finger nucleases: the next generation emerges." *Mol Ther* 16(7): 1200-7.
Durai, S., M. Mani, et al. (2005). "Zinc finger nucleases: custom-designed molecular scissors for genome engineering of plant and mammalian cells." *Nucleic Acids Res* 33(18): 5978-90.
Gaur, M. and A. D. Leavitt (1998). "Mutations in the human immunodeficiency virus type 1 integrase D,D(35)E motif do not eliminate provirus formation." *J Virol* 72(6): 4678-85.
Gotoh, O. (1982). "An improved algorithm for matching biological sequences." *J Mol Biol* 162(3): 705-8.
Hacein-Bey-Abina, S., A. Garrigue, et al. (2008). "Insertional oncogenesis in 4 patients after retrovirus-mediated gene therapy of SCID-X1." *J Clin Invest* 118(9): 3132-42.
Hacein-Bey-Abina, S., C. von Kalle, et al. (2003). "A serious adverse event after successful gene therapy for X-linked severe combined immunodeficiency." *N Engl J Med* 348(3): 255-6.
Honma, M., M. Izumi, et al. (2003). "Deletion, rearrangement, and gene conversion; genetic consequences of chromosomal double-strand breaks in human cells." *Environ Mol Mutagen* 42(4): 288-98.
Honma, M., M. Sakuraba, et al. (2007). "Non-homologous end-joining for repairing I-Scel-induced DNA double strand breaks in human cells." *DNA Repair (Amst)* 6(6): 781-8.
Howe, S. J., M. R. Mansour, et al. (2008). "Insertional mutagenesis combined with acquired somatic mutations causes leukemogenesis following gene therapy of SCID-X1 patients." *J Clin Invest* 118(9): 3143-50.
Kent, W. J. (2002). "BLAT—the BLAST-like alignment tool." *Genome Res* 12(4): 656-64.
Kim, Y. G., J. Cha, et al. (1996). "Hybrid restriction enzymes: zinc finger fusions to Fok I cleavage domain." *Proc Natl Acad Sci USA* 93(3): 1156-60.
Li, L., J. M. Olvera, et al. (2001). "Role of the non-homologous DNA end joining pathway in the early steps of retroviral infection." *EMBO J* 20(12): 3272-81.
Lombardo, A., P. Genovese, et al. (2007). "Gene editing in human stem cells using zinc finger nucleases and integrase-defective lentiviral vector delivery." *Nat Biotechnol* 25(11): 1298-306.
Mani, M., J. Smith, et al. (2005). "Binding of two zinc finger nuclease monomers to two specific sites is required for effective double-strand DNA cleavage." *Biochem Biophys Res Commun* 334(4): 1191-7.
Miller, D. G., L. M. Petek, et al. (2004). "Adeno-associated virus vectors integrate at chromosome breakage sites." *Nat Genet* 36(7): 767-73.
Miller, J. C., M. C. Holmes, et al. (2007). "An improved zinc-finger nuclease architecture for highly specific genome editing." *Nat Biotechnol* 25(7): 778-85.
Modlich, U., J. Bohne, et al. (2006). "Cell-culture assays reveal the importance of retroviral vector design for insertional genotoxicity." *Blood* 108(8): 2545-53.
Montini, E., D. Cesana, et al. (2006). "Hematopoietic stem cell gene transfer in a tumor-prone mouse model uncovers low genotoxicity of lentiviral vector integration." *Nat Biotechnol* 24(6): 687-96.
Nightingale, S. J., R. P. Hollis, et al. (2006). "Transient gene expression by nonintegrating lentiviral vectors." *Mol Ther* 13(6): 1121-32.
Ott, M. G., M. Schmidt, et al. (2006). "Correction of X-linked chronic granulomatous disease by gene therapy, augmented by insertional activation of MDS1-EVI1, PRDM16 or SETBP1." *Nat Med* 12(4): 401-9.
Perez, E. E., J. Wang, et al. (2008). "Establishment of HIV-1 resistance in CD4+ T cells by genome editing using zinc-finger nucleases." *Nat Biotechnol* 26(7): 808-16.
Porteus, M. H. and D. Carroll (2005). "Gene targeting using zinc finger nucleases." *Nat Biotechnol* 23(8): 967-73.
Schmidt, M., K. Schwarzwaelder, et al. (2007). "High-resolution insertion-site analysis by linear amplification-mediated PCR (LAM-PCR)." *Nat Methods* 4(12): 1051-7.
Smith, T. F. and M. S. Waterman (1981). "Identification of common molecular subsequences." *J Mol Biol* 147(1): 195-7.

Szczepek, M., V. Brondani, et al. (2007). "Structure-based redesign of the dimerization interface reduces the toxicity of zinc-finger nucleases." *Nat Biotechnol* 25(7): 786-93.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

FIGURE LEGENDS

FIG. 1: Comparative analysis of off-site sequence homologies. The sequences of the 11 most likely off-site regions have been aligned using the sequence logo generator WebLogo (weblogo.berkeley.edu/).

Figure 2:
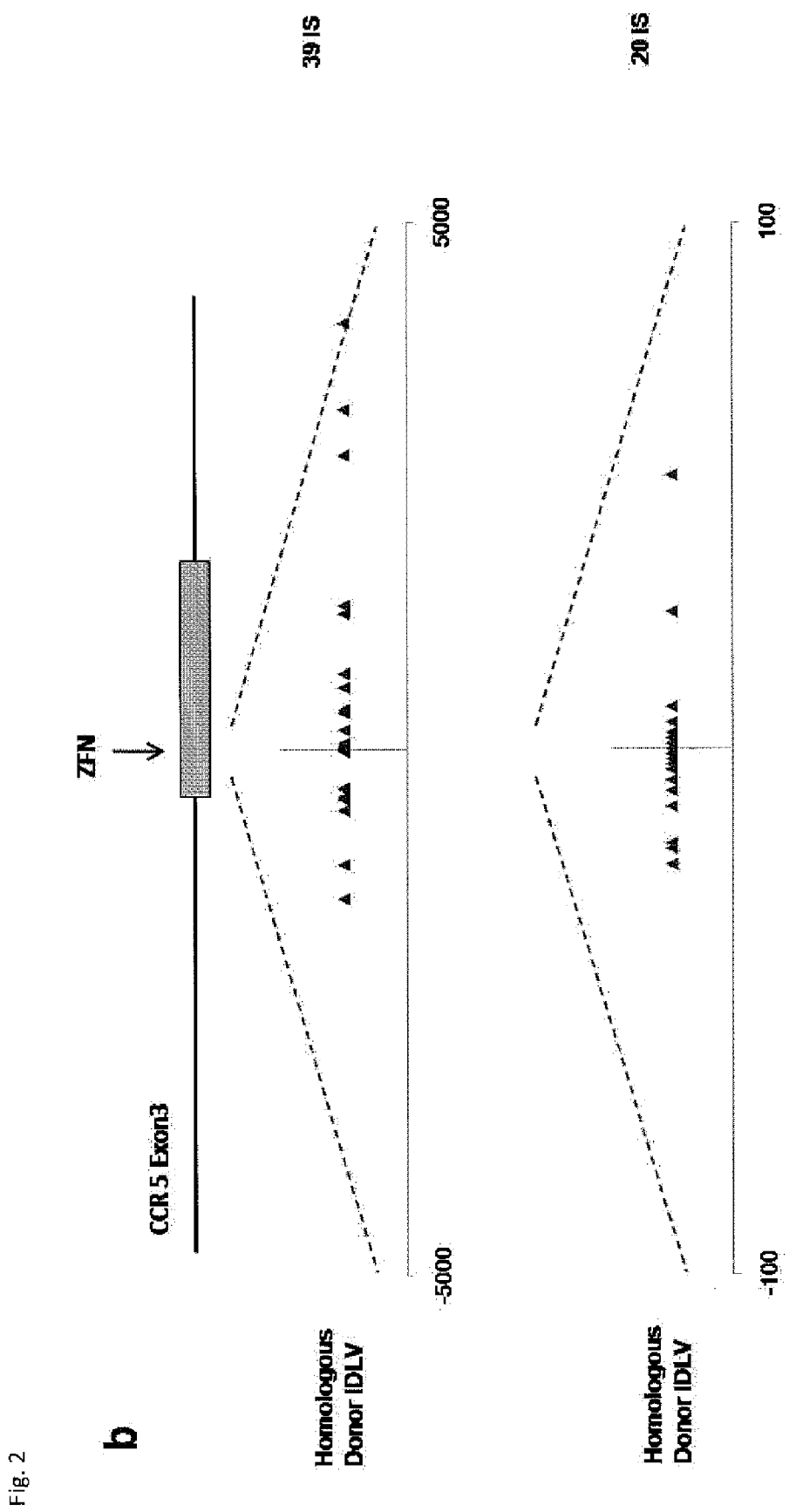

FIG. 2: Insertion site distribution in K552 cells Coinfected with CCR5 targeting ZFN expressing IDLV and a donor IDLV containing homology regions to the target site., a) Genome wide location of IDLV identified by LAM-PCR. Blue triangles indicate distribution of 208 IS from two ZFN and donor IDLV treated samples, blue bars show location of IDLV integrants in a sample treated with the donor IDLV alone. b) Insertion sites located in Exon 3 of the CCR5 gene.

Figure 3A:
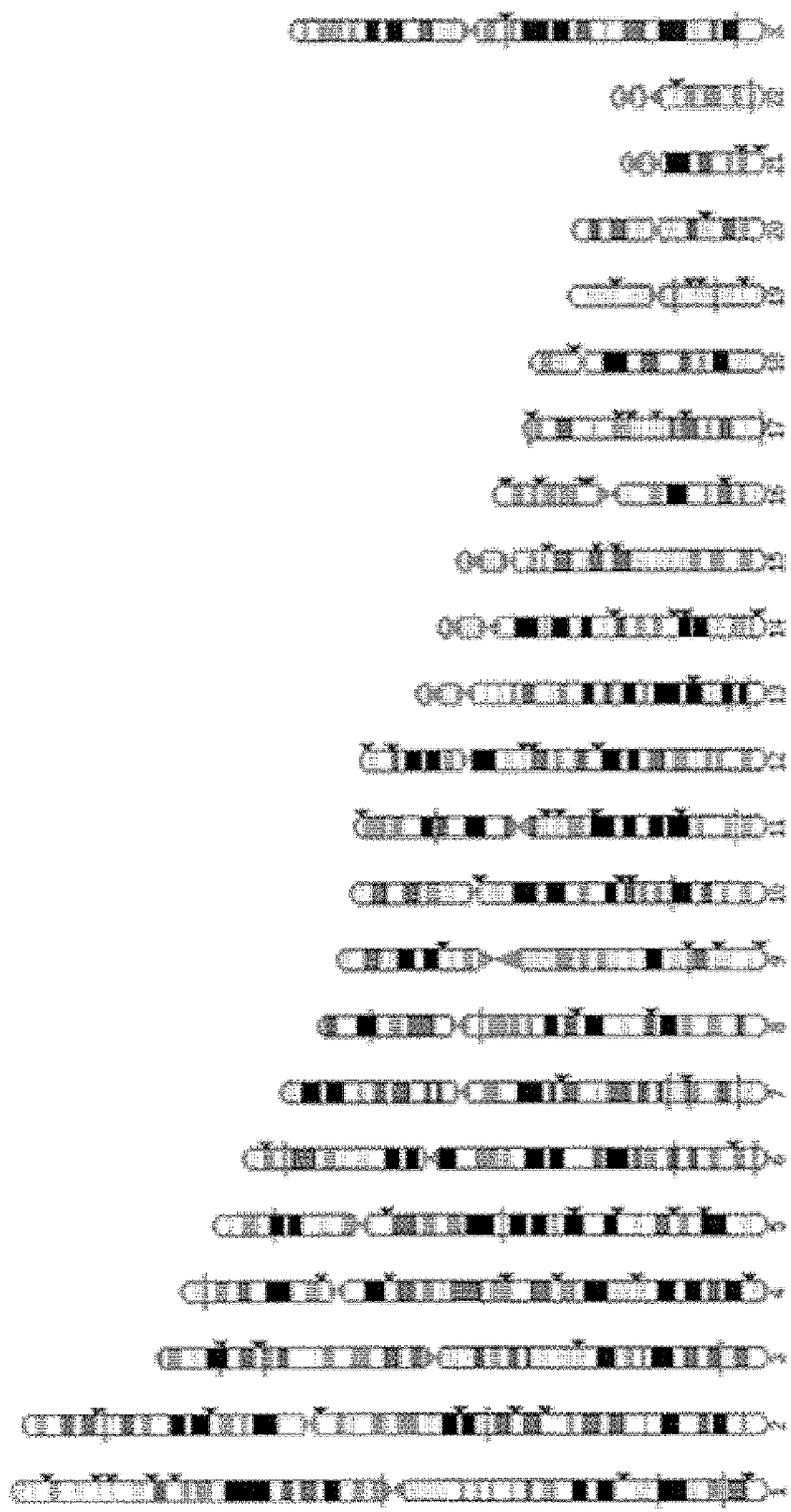

FIG. 3: Insertion site distribution in K562 cells coinfected with IL2RG targeting ZFN expressing IDLV and a donor IDLV containing homnology regions to the IL2RG target site. a) Genome wide location of IDLV identified by LAM-PCR. Red triangles indicate distribution of 96 IS from three GFP positive sorted samples, coinfected with ZFN expressing IDLV and donor IDLV. Red bars show the genomic locations of 37 IDLV IS in a sample treated with solely the donor IDLV. b) Location of the insertion sites in Exon 5 of the IL2RG gene.

Figure 4A:
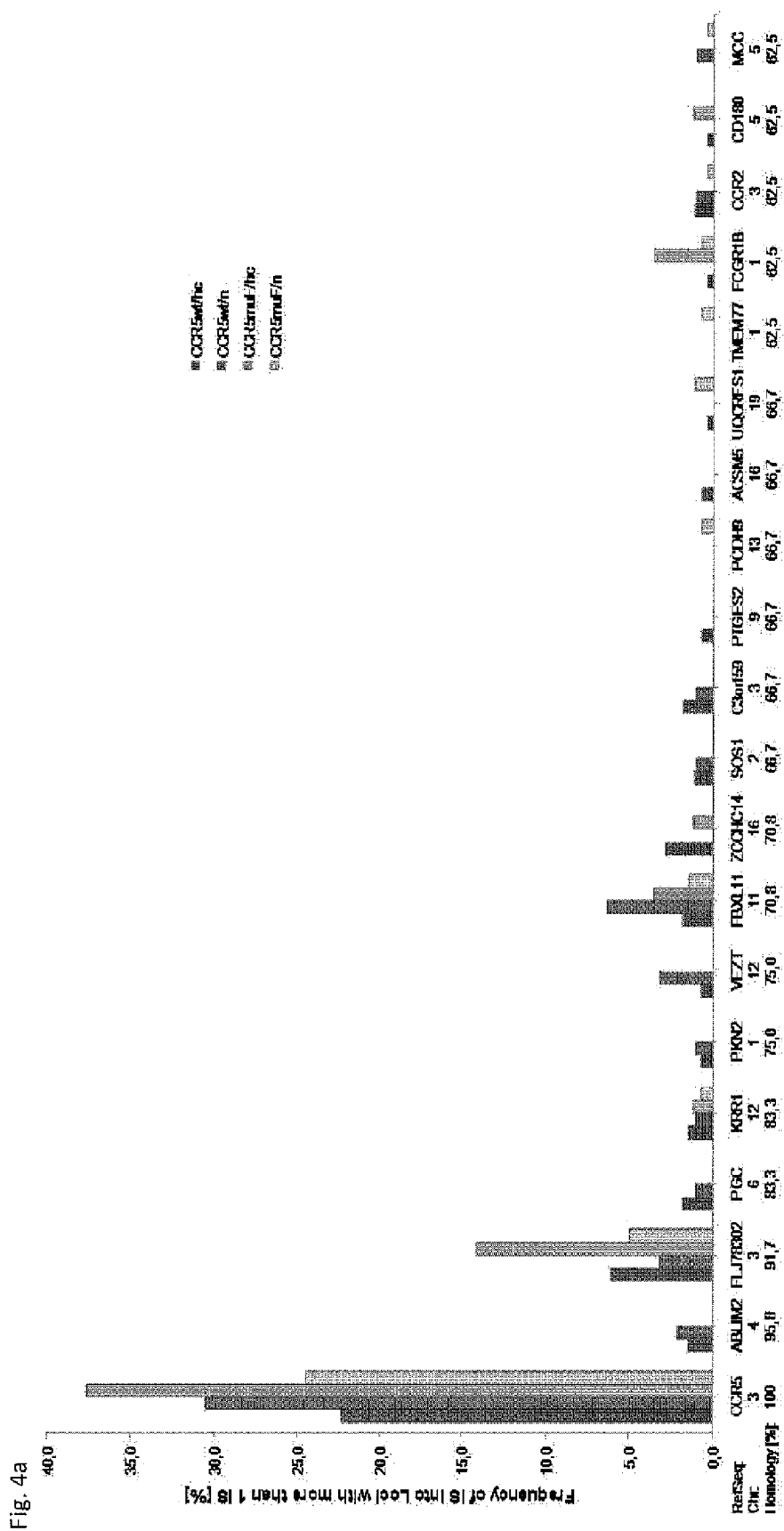
Figure 4B:
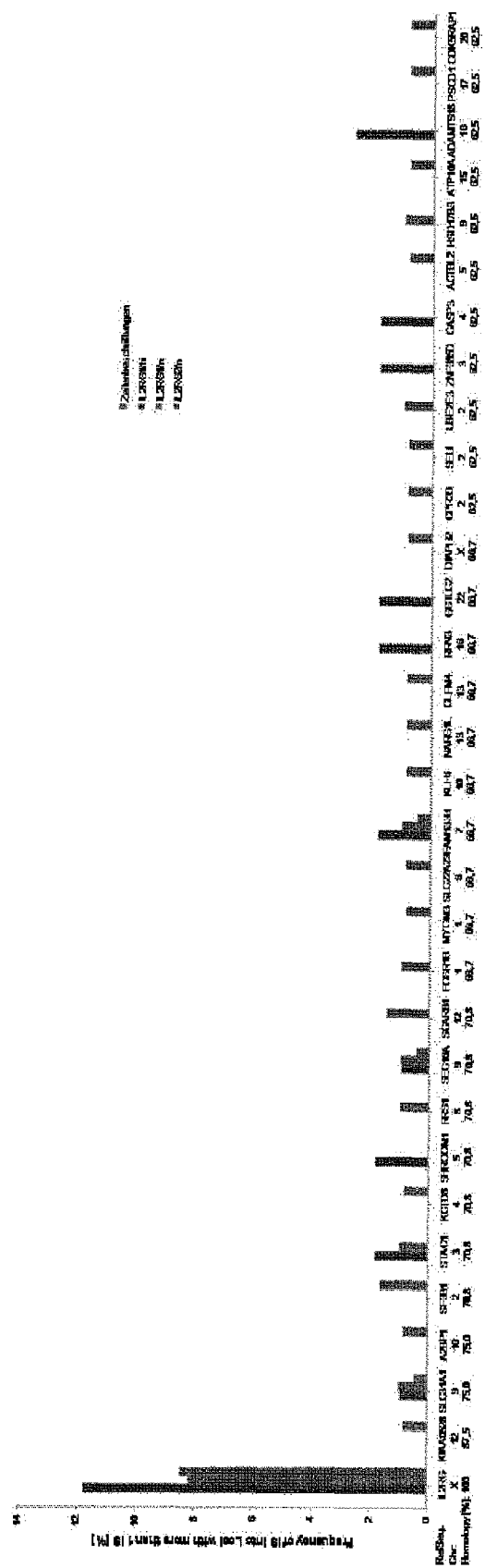

FIG. 4: Number of IS into the same genomic region in ZFN treated cells. (a) Genomic regions which have been found to harbor multiple IS in the different cells treated with the CCR5 targeting ZFN are shown. (b) Regions with more than one Integration in IL2RG-ZFN treated cells. Percentages below the RefSeq gene name show the identity between the original ZFN target site and the off-target site.

Figure 5:
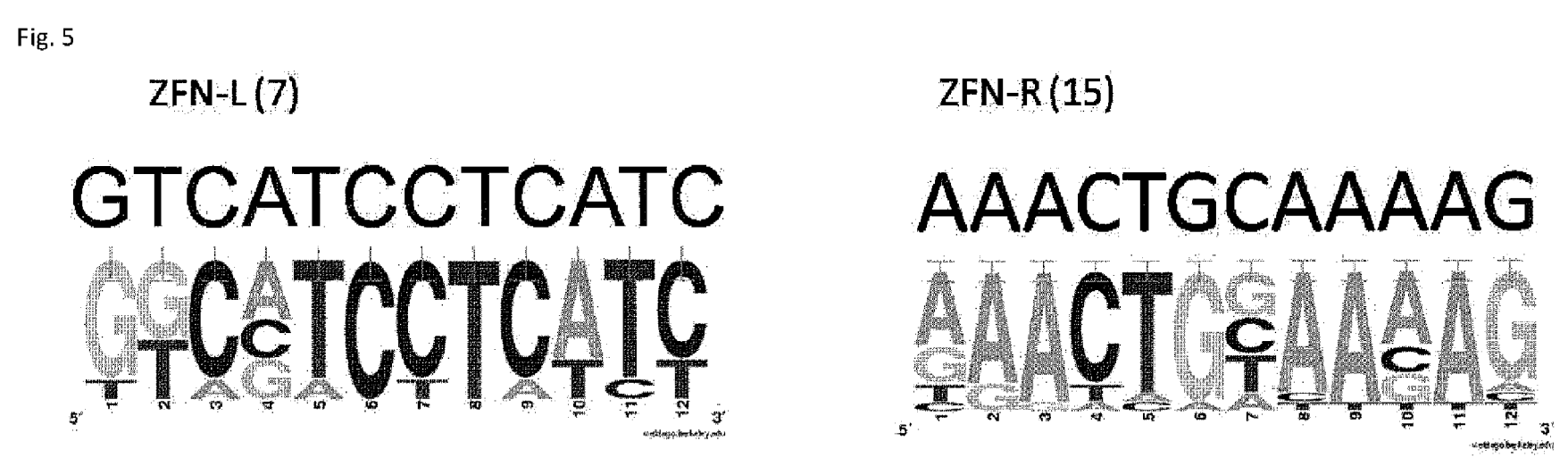

FIG. 5. Comparison of off-site sequences of zinc finger motifs.

EXAMPLES

Example 1

IDLV Integration as a Stable Marker for DSB

To analyze whether IDLV are captured into preexisting DSB similar to what has been described for AAV derived vectors (Miller et al. 2004) and therefore can serve as a stable genetic marker for the temporary DSB, we introduced multiple DSB by gamma-irradiation in K562 cells and determined the frequency of integrated vector forms. K562 cells transduced with a GFP expressing IDLV prior to irradiation (48 hours after transduction) showed a frequency of GFP positive cells of 82.5% on day 5 after transduction, whereas non-irradiated cells revealed 68.7% GFP positive cells. 20 days after IDLV transduction 13.5% of the gamma-irradiated cells were still GFP positive, whereas only 6.2% of the non-irradiated cells showed GFP expression. These levels sustained for the whole observation period (35 days), an observation well in line with an increase in the frequency of IDLV integrations that are not diluted out by cell division (FIG. 1).

We analyzed the residual integration pattern of an IDLV carrying the D64V mutation in the viral integrase in transduced K562 cells (Donor$_u$). Lentivirus integration sites (IS) of the IDLV in the cellular genome were studied by LAM-PCR (Schmidt et al. 2007) and nrLAM-PCR (Gabriel et al. 2009). Analysis of more than 100 IS from IDLV$_n$ transduced K562 cells (as well as ~500 IDLV IS obtained from other cell lines showed a close to random integration profile with no obvious preference of insertion into gene coding regions or other genomic structures of the human genome, contrary to what has been described for ICLV (FIG. 1). Small deletions (<24 bp) of the LTR were detectable in 20% of these sequences, which occurs only rarely in ICLV transduced cells. This may indicate that NHEJ is involved in IDLV insertions into DNA DSB.

Example 2

IDLV Marked DSB are Overrepresented in the Target Site after ZFN Application

To examine whether the integration pattern of IDLV changes after ZFN treatment, we analyzed IS in K562 cells infected with IDLV expressing ZFN either targeting Exon 3 of the CCR5 gene locus or Exon 5 of the IL2RG gene locus. These cells were co-infected with a non-integrating donor vector harboring a GFP expression cassette under control of the human PGK promoter, flanked by regions homologous to the respective target site (CCR5$_{wt/hc}$ or IL2RG$_{1/hi}$, respectively). We had previously shown the targeted integration of the PGK-GFP expression cassette by HR in up to 50% in these cells (Lombardo et al. 2007).

We identified IDLV integrations by unbiased nrLAM and/or LAM-PCR optimized for accessing a large portion of the human genome by using the enzymes HpyCH4V, MseI, Tsp509I or MspI.

Deep sequencing of the amplified IDLV-genome junctions revealed 282 unique lentivirus LTR insertions in CCR5$_{wt/hc}$ samples. These IS were distributed throughout the genome (FIG. 2a) but strikingly, 59 out of these 282 IS (20.9%) could be mapped to Intron2 or Exon 3 of the CCR5 gene, located 1.4 kb to 2.7 kb up- or downstream of the ZFN target site (FIG. 2b). 30 of those 59 IS in the CCR5 gene were clustered at most 52 nucleotides apart from the ZFN binding site. These data indicate that IDLV integration at the specific ZFN target site resulted from NHEJ repair, which is known to introduce mainly small deletions of <60 bp, but also deletions up to 4 kb have been described (Honma et al. 2003; Honma et al. 2007).

Additionally, we analyzed the same ZFP fused to the recently described obligate heterodimeric FokI nuclease domain (Miller et al. 2007). In cells treated with this advanced ZFN architecture, we detected 85 IDLV integrations in samples coinfected with the CCR5 homologous donor vector (CCR5$_{muF/hc}$). Of those, 32 IS (37.6%) were located closer than 1.9 kb distance to the ZFN target site in the CCR5 gene, most of them (24 IS) within a 60 bp window surrounding the target site.

Insertion site analysis of cells transduced only with the IDLV donor vector harboring homologous sequences to the CCR5 target site (IDLV$_{hc}$) in absence of the CCR5 targeting ZFN revealed 66 IS, 4 (6.1%) of them located within the CCR5 gene. These IS were located between 388 bp upstream and 988 bp downstream of the target locus, most likely representing spontaneous homologous recombination events (FIG. 2b).

In the case of the $IL2RG_{1/hi}$ approach, LAM PCR revealed 111 different genomic IDLV insertion loci, of which 13 (11.7%) mapped to the IL2RG locus, at most 1.1 kb apart from the ZFN target locus. Eight of these 13 IS were located within 16 bp distance to the ZFN target site (FIG. 3). Also here, we detected 3 out of 46 IS (6.5%) located in Intron 4 of the IL2RG gene, 235 to 611 bp downstream of the target site in one sample which has been treated with the IL2RG—homologous donor vector ($IDLV_{hi}$) in absence of ZFN (FIG. 3b).

Example 3

Integration of IDLV into the CCR5 and IL2RG Target Site is Mediated by NHEJ

To analyze the proportion of ZFN induced off-target DSB more precisely, we sought to eliminate the possibility of HR competing with NHEJ. We repeated and expanded our analyses in K562 cells coinfected with CCR5- or IL2RG specific ZFN-expressing IDLV and a donor IDLV without any homology regions to either target site. Due to the lack of homology between donor IDLV and target locus, integration of the GFP expression cassette could not be attributed to HR. Therefore IDLV should be captured sequence independent into any DSB through NHEJ. (nr)LAM-PCR analysis of $CCR5_{wt/n}$, samples showed 95 IS from which 29 (30.5%) mapped to the CCR5 locus. 26 of these IS were located closer than 55 bp apart from the ZFN target site.

Insertion site analysis of the samples treated with CCR5 specific ZFP fused to the mutated obligate heterodimeric FokI nuclease domain revealed 290 IS in samples coinfected with the nonhomologous donor vector ($CCR5_{muF/n}$). 71 (24.5%) of these IS were not exceeding 3.1 kb to the ZFN target site, whereas 52 IS were positioned within a 60 bp window surrounding the target site.

For the IL2RG targeting ZFN, we compared two different sets of zinc finger proteins. By (nr)LAM-PCR analysis we detected 208 IS in the $IL2RG_{1/n}$ setting, from which 17 IS (8.2%) mapped to the target locus. From the $IL2RG_{2/n}$ setting we retrieved 248 IS, from which 21 (8.5%) mapped to the target locus. These "on-target" IS were located at most at 585 bp distance to the site were the ZFN induced DSB is expected.

As a reminder, none of the IS obtained from the samples treated with the nonhomologous donor IDLV ($IDLV_n$) alone was located in the vicinity to the CCR5 or IL2RG target site.

Example 4

Location of the Detected Off-Site Integration in ZFN Treated Cells

Out of the 377 unique IS retrieved from $CCR5_{wt/hc}$ and $CCR5_{wt/n}$ samples, on top of the 88 IS located within the CCR5 gene 80 additional IS were located in 13 different chromosomal regions, each of these loci carrying more than one integrated IDLV (FIG. 4). Such integrations with common locations have been found within the same sample but also between independently transduced cell populations. In some cases, the IDLV insertions were located in a very close distance to each other (0-60 bp), but also distances up to 260 bp between two IS have been found (FIG. 4a and Table 2).

In the samples transduced with the obligate heterodimeric FokI ZFN ($CCR5_{muF/hc}$ and $CCR5_{muF/n}$), 49 of the 375 IS identified by LAM-PCR have been found to be located in 7 other chromosomal loci separate from the CCR5 ZFN target site, each of them harboring at leastmore than 2 closely related IS (FIG. 4a and Table 2). Four of these loci, namely FLJ78302, KRR1, FBXL11 and ZCCHC14 have been found to harbor at least one IDLV integrant in the sample transduced with the mutated FokI as well as the WT FokI domain.

For the $IL2RG_{1/hi}$ and $IL2RG_{1/n}$ samples, we could identify 38 out of 318 IS in 15 genomic loci outside the target region, which itself harbored 30 IS. Each of these loci carried two to four IDLV insertions (Table 3). As integrations into such small regions are very unlikely to occur by chance, genomic loci which carry more than 1 IS in a very close proximity to each other may represent potential off-target hotspots for the respective ZFN.

Out of the 248 IS for the $IL2RG_{2/n}$ setting 32 IS were detected in 15 chromosomal loci, which harbored more than one IDLV integrant in close proximity. Three of these loci (FAM133B, SLC31A1 and SEC16A) harbored integrations in $IL2RG_{1/n}$ and $IL2RG_{2/n}$ samples and SEC16a had also an integration event in the $IL2RG_{1/hi}$ transduced cells (Table 3).

Example 5

Partial Target Sequence Homologies Determine the Likelihood of ZFN Induced DSB

We hypothesized that if ZFN target fidelity was substantial, off-target restriction of the ZFN should most likely affect the sequences of the genome most homologous to the original target motif. An in silico search of the human genome for possible off-target sites of ZFN action on the basis of sequence similarity to the intended target site of the ZFN heterodimer allowed to rank sequences most likely to be subject to cleavage by ZFN. As ZFN dimerization is most effective if the binding sites of the ZFN monomers are separated by 5-6 nucleotides, we searched for off-target binding sites allowing spacing of ZFN monomers between 0-10 nucleotides. In addition to the intended heterodimerization of two different ZEN monomers, we also searched for genomic sites supporting the formation of homodimers from each of the two ZFN monomers. The human genome does indeed contain numerous of these theoretical in silico off-target loci, which show only few mismatches to either target site. However, partial sequence homology is found to be more abundant for the CCR5 target site. Table 1 lists all genomic sites with partial homology to the ZFN target sites with at most two (CCR5) or three (IL2RG) mismatching nucleotides. From this top list with only minor differences to the target site, IDLV insertions have been detected in the ABLIM2 gene (4 IS) and in the CCR2/FLJ78302 gene (41 IS), both previously described known off-target sites of the CCR5 specific ZFN (Perez et al. 2008). These off-site motifs show 96 or 92% sequence similarity to the CCR5 target site, respectively. In case of the IL2RG specific ZFN, 2 IS had been detectable by LAM-PCR in the KIAA0528 gene (88% sequence homology to the target site). To determine the accuracy of our in silico modeling, we compared our data with the real IS identified by LAM PCR. Strikingly, we indeed found 150 IS in 66 loci where an integration event of the IDLV occurred within a 150 bp distance to a partially homologous ZFN target site, with more than 70.8% sequence similarity to the original CCR5 target site (Table 2). In cells treated with the IL2RG specific ZFN, 45 genomic loci with partial sequence homology to the target site carried 63 IDLV integrants in total (Table 3).

Example 6

Deep-Sequencing of Potential Off-Site Hotspots

To quantify the ZFN activity at the most likely off-site loci, we sequenced 15 genomic loci per ZFN target system by pyrosequencing after exposure to the different ZFN described above. These Loci were chosen based on the presence of a partial homologous target site in the vicinity of a identified IS or for the reason that more than 1 IS has been detected in this locus. After high-throughput sequencing of the amplified loci the obtained sequences have been analysed for signs of NHEJ, namely small insertions or deletions at these loci.

Example 7

In Vivo ZFN Binding Assay

To determine the sequence binding specificity of the different ZFP, we aligned the 11 most probable binding sites of the identified off target Loci. This comparative analysis of off-site sequence homologies allows to rapidly optimize zinc finger motifs (FIG. 5).

Example 8

Methods

γ-Irradiation of IDLV Transduced K562 Cells $1 \times 10^4$ K562 cells were seeded into a 12-well plate and transduced with a GFP expressing LV 24 h later with 0.6 µg HIV-1 gag p24. Cells have been γ-irradiated with 2.5 Gy 48 h after transduction. GFP expressing cells were counted by FACS for further 34 days.

Insertion Site Analysis by LAM-PCR.

To identify insertion sites of the IDLV LAM-PCR was performed as previously described using the enzymes Tsp509I, MseI, HpyCH4V and MspI (Schmidt et al. 2007). In brief, genomic DNA from transduced cell samples was preamplified by linear PCR using LTR-specific biotinylated primers. PCR products were captured on solid phase by magnetic beads (Dynabeads). After synthesis of the second strand, restriction digest of ds DNA and ligation of a linker cassette two additional rounds of exponential nested PCRs were performed. The resulting amplicons were sequenced using the Roche/454 platform and sequences obtained were aligned to the human genome via BLAT (BLAST like alignment tool) (Kent 2002)

Pyrosequencing Using the 454 Platform (Roche).

PSR amplicons were prepared as suggested by the manufacturer. An additional PCR ('Fusionprimer-PCR') with fusionprimers containing individual barcode sequences of 6 bases was carried out. 40 ng of purified LAM-PCR products served as template for the fusionprimer PCR reaction. PCR conditions: Initial denaturation 2 minutes at 95° C.; followed by 12 cycles at 95° C. for 45 s, 60° C. for 45 s and 72° C. for 60s. Final elongation was 5 minutes at 72° C. 15 µl of the PCR-products were analysed on a 2% agarose gel. DNA concentration was measured with the ND-1000 Spectrophotometer (Thermo Scientific).

IS Data Analysis of IDLV Transduced

LAM-PCR amplicon sequences have been identified through sequence alignment using BI2Seq (Altschul et al. 1990) and the Smith-Waterman algorithm (Smith and Waterman 1981; Gotoh 1982). After trimming, the sequences were aligned to the human genome using the assembly from UCSC (RefSeq genes and RepeatMasker; Alignment March 2006). IS were considered as valid if a LTR-genome junction was present and the flanking genomic region showed a unique sequence match of at least of 95% after alignment to the human genome using BLAT (Kent 2002)

In Silico Prediction of Off-Target Loci

In order to identify sequence parts homologous to the ZFN motives, the human genome was scanned for all possible 3mers contained in the ZFN motives. All matches were extended to full motive length depending on the location of the 3mer within the motive. Between the two ZFN cassettes a possible spacer from 0 to 10 nucleotides was considered. Consent was displayed in capital letters while mismatches with the ZFN motive were reported in lowercase. The information about the homologs was directly linked to the IS for further analyses.

TABLES

TABLE 1

Theoretical off-target hotspots based on sequence similarities to the ZFN binding sites. Green hooks indicate an overlap between theoretical predicted off-site loci and experimentally derived IS by LAM-PCR.

| Konfiguration | Chromosome | Off-site Locus | Target Sequence | Match | Identity [%] | RefSeq | | SEQ ID NO |
|---|---|---|---|---|---|---|---|---|
| ZFN-L_N5_ZFN-R | 3 | 46389562 | GTCATCCTCATCctgatAAACTGCAAAAG | 24 | 100.0 | CCR5 | ⊙ | 1 |
| ZFN-L_N5_ZFN-L | 4 | 8165389 | GTCATCCTCATCtcacgGATGAGGATGcC | 23 | 95.8 | ABLIM2 | ⊙ | 2 |
| ZFN-R_N6_ZFN-R | 14 | 87308775 | gTTTTGCAGTTTcacctcAAACTGCAAAAG | 23 | 95.8 | GALC | | 3 |
| ZFN-L_N6_ZFN-R | 3 | 46374223 | GTCgTCCTCATCttaatAAACTGCAAAAa | 22 | 91.7 | FLJ78302/CCR2 | ⊙ | 4 |
| ZFN-R_N6_ZFN-R | 21 | 32319982 | gTTTTGCtGTTTcagcttAAACTGCAAAAG | 22 | 91.7 | HUNK | | 5 |
| ZFN-R_N6_ZFN-R | 8 | 78368449 | gTTTTGCtGTTTcacctaAAACTGCAAAAG | 22 | 91.7 | PXMP3 | | 6 |
| ZFN-R_N6_ZFN-R | 17 | 64617769 | CTTTTGCtGTTTgcacctcAAACTGCAAAAG | 22 | 91.7 | ABCA6 | | 7 |
| ZFN-R_N8_ZFN-R | 4 | 17039123 | aTTTTGCAGTTTtgtcattcAAACTG-CAAAtG | 22 | 91.7 | QDPR | | 8 |
| ZFN-L_N7_ZFN-R | 14 | 64097852 | GTCATCCcCATCagggtacAAtCTGCAAAAG | 22 | 91.7 | C14orf50 | | 9 |

TABLE 1-continued

Theoretical off-target hotspots based on sequence similarities to the ZFN binding sites. Green hooks indicate an overlap between theoretical predicted off-site loci and experimentally derived IS by LAM-PCR.

Top off sites IL2RG

| Konfiguration | Chromosome | Off-Site Locus | Target sequence | Match | Identity [%] | RefSeq | SEQ ID NO |
|---|---|---|---|---|---|---|---|
| ZFN-L_N5_ZFN-R | X | 70245876 | CTTCCACAGAGTgggttAAAGCGGCTCCG | 24 | 100 | IL2RG | 10 |
| ZFN-L_N4_ZFN-L | 2 | 95716757 | CTTCCACAGAGTgcctACTCTGTGtcAG | 22 | 92 | TRIM43 | 11 |
| ZEN-L_N8_ZFN-L | 6 | 51070975 | CTTCCACAGAGTcatttcccgCTCTtcG-GAAG | 21 | 88 | TFAP2B | 12 |
| ZFN-L_N8_ZFN-L | 18 | 47472499 | CTTCtACAGAGccggcgtacACTCTGTG-GAtG | 21 | 88 | MEX3C | 13 |
| ZFN-L_N8_ZFN-L | 10 | 133619910 | CTTCCtCcGAGTccaggtggACTCTGTG-GAtG | 21 | 88 | PPP2R2D | 14 |
| ZEN-L_N8_ZFN-L | 6 | 169388271 | CTTCCACAGAGTttttcaaacACTagGTG-GAcG | 21 | 88 | THBS2 | 15 |
| ZEN-L_N7_ZPN-L | 9 | 125928116 | CTTCCAgAGAGcaaccccccACTCTtTGGAAG | 21 | 88 | LHX2 | 16 |
| ZEN-L_N8_ZFN-L | 12 | 113537261 | CagCCAgAGAGTcactggtcACTCTGTG-GAAG | 21 | 88 | TBX3 | 17 |
| ZEN-L_N6_ZFN-L | 2 | 188445229 | CTTCCACtGtGTcctagaACTCTGTGcAAG | 21 | 88 | TFPI | 18 |
| ZEN-L_N7_ZFN-L | 7 | 118347037 | CTTCCACAGAaaattccgACTCTcTGGAAa | 21 | 88 | ANKRD7 | 19 |
| ZFN-L_N5_ZFN-L | 11 | 127323200 | CTTCCACAcAGTggtattCTCTaTGGAAG | 21 | 88 | ETS1 | 20 |
| ZFN-L_N5_ZFN-L | 12 | 22563143 | CTTCCAtAtAGTtagagACTCTGTGGcAG | 21 | 88 | KIAA0528 | 21 |
| ZFN-L_N4_ZFN-L | 2 | 113803869 | CTTCCACAGgGTgcctACTCTGTGtcAG | 21 | 88 | PAX8 | 22 |

TABLE 2

| RefSeq | ChrMatch | Identify [%] | OS Locus | Configuration | Motif Sequence | Samples | No. of IS | Region of IS | Distance to Motif | SEQ ID NO |
|---|---|---|---|---|---|---|---|---|---|---|
| ABLIM2 | 4 | 23 | 95.8 | 8165391 | L_5_L | GTCATCCTCATCtcacgGATGAGGATGcC | CCR5muF/hc-2;CCR5wt/hc-1 | 4 | 8165369-8165401 | 2-22 | 140 |
| FLJ78302 | 3 | 22 | 91.7 | 46374224 | L_5_R | GTCgTCCTCATCttaatAAACTGCAAAAa | CCR5muF/hc-1;CCR5muF/hc-2; CCR5muF/n-1;CCR5muF/n-2; CCR5muF/n-3;CCR5muF/hc-1; CCR5muF/hc-2;CCR5wt/hc-1; CCR5wt/hc-4;CCR5wt/hc-1; CCR5wt/n-2 | 41 | 46374176-43674245 | 1-48 | 141 |
| MRPL22 | 5 | 21 | 87.5 | 154350452 | L_5_L | aTCATCCTCATCttgcaGATGAGGgaGAC | CCR5wt/hc-4 | 1 | 154350453 | 2 | 23 |
| VPS8 | 3 | 21 | 87.5 | 185963705 | L_6_L | GTCATCCTCATCtcatccATGAGGAaGAg | CCR5muF/hc-1 | 1 | 185963805 | 100 | 24 |
| VPS8 | 3 | 18 | 75.0 | 185963705 | L_6_R | GTCCTCCTCATCtcatccAtgaGgAagAG | CCR5muF/hc-1 | 1 | 185963805 | 100 | 142 |
| DDX10 | 11 | 20 | 83.3 | 108275348 | R_5_R | CTTTTgCAGTTtaaaaAAACAgAAAAG | CCR5muF/hc-1 | 1 | 108275350 | 3 | 25 |
| KRR1 | 12 | 20 | 83.3 | 74249732 | R_5_L | CaTTTcCAGTTTaaagaGATGAGGAgcC | CCR5muF/hc-1;CCR5muF/n-3; CCR5muF/hc-2;CCR5wt/hc-1; CCR5wt/hc-4;CCR5wt/hc-1; CCR5wt/n-2 | 6 | 74249709-74249748 | 2-23 | 26 |
| PGC | 6 | 20 | 83.3 | 41813540 | R_5_R | CTgTTacCAGTTtcacgagAAACTGCAAgAG | CCR5wt/hc-1;CCR5wt/hc-2; CCR5wt/n-1 | 6 | 41813533-41813551 | 1-12 | 27 |
| FAM27L | 17 | 19 | 79.2 | 21807089 | R_3_R | CTTTTtCAGTTTcccAAACTGaAActc | CCR5muF/n-3 | 1 | 21806997 | 92 | 28 |
| FARP1 | 13 | 19 | 79.2 | 97605112 | R_5_L | CTTTTgCAGTTTctgtGgTGAGGActtt | CCR5muF/hc-2 | 1 | 97605115 | 4 | 29 |
| FBLIM1 | 1 | 19 | 79.2 | 15970643 | R_3_R | CTTTTgCAGTTTatgtAAgcTGCAttct | CCR5muF/hc-1 | 1 | 15970643 | 1 | 30 |
| GPR158 | 10 | 19 | 79.2 | 25432826 | L_5_R | GTagTCCTCcTTCctgctaAACTGCAttgG | CCR5muF/hc-2 | 1 | 25432830 | 5 | 31 |
| LPHN2 | 1 | 19 | 79.2 | 81568853 | L_5_L | catcTCatCATCatGATGAGGATGAC | CCR5muF/hc-1 | 1 | 81568446 | 7 | 32 |
| MRPS9 | 2 | 19 | 79.2 | 105096447 | L_5_L | CTTTTgCAGTTTagacaAAACTGCccgc | CCR5muF/hc-1 | 1 | 105096448 | 2 | 33 |
| NEBL | 10 | 19 | 79.2 | 21560894 | R_10_L | CTTTTgCggTTtatacaactgATcAG-cATTAg | CCR5muF/hc-1 | 1 | 21560893 | 1 | 34 |
| TBC1D4 | 13 | 19 | 79.2 | 74565440 | L_5_L | aattTCCTCATCtgaaaGAcGAGGATGAC | CCR5wt/hc-1 | 1 | 41565437 | 3 | 35 |
| ACSF2 | 17 | 18 | 75.0 | 45851909 | R_10_R | CTTTTaCAGTTTaccaccaaaacAgAaT-caAAAAc | CCR5wt/hc-2 | 1 | 45851903 | 6 | 36 |
| C3orf56 | 3 | 18 | 75.0 | 128457777 | R_4_R | CTTTTTtCAGTTaatctActCTgGAAAAG | CCR5wt/hc-1 | 1 | 128457779 | 2 | 37 |
| IL1RAPL1 | X | 18 | 75.0 | 28670165 | R_4_L | aTTTTGCAGTaTggaaaATGActATGcC | CCR5wt/hc-1 | 1 | 28670265 | 100 | 38 |
| JHDM1D | 7 | 18 | 75.0 | 139454703 | R_0_L | CcTTTTGgtcTTTGATGAtGgTGAC | CCR5wt/n-1 | 1 | 139454799 | 96 | 39 |
| KIAA0195 | 17 | 18 | 75.0 | 71002995 | L_0_L | cTTcTCCTCATgGAgGAGGAggGC | CCR5wt/hc-2 | 1 | 71002993 | 2 | 40 |
| KSP37 | 10 | 18 | 75.0 | 46659954 | L_5_R | GTTATCaCCATCccaatAAACTGCAcAtt | CCR5wt/hc-2 | 1 | 44659667 | 114 | 41 |
| MGAT4A | 2 | 18 | 75.0 | 98606670 | R_3_R | CgTTTTGCACTTTgtaAcAcCACAgG | CCR5muF/n-1 | 1 | 98606586 | 84 | 42 |
| PKN2 | 1 | 18 | 75.0 | 88422189 | R_7_R | gTTTatCATTTCtttataAAACTGtAAAAG | CCR5wt/hc-1;CCR5wt/hc-2 | 3 | 88422182-88422203 | 1-15 | 43 |
| POU6F2 | 7 | 18 | 75.0 | 39226321 | R_6_R | CacTTcCAGTTTattatgAAACCgtgAAAG | CCR5wt/n-2 | 1 | 39226320 | 1 | 44 |
| TBC1D4 | 13 | 18 | 75.0 | 74848856 | R_5_R | CTTTTaCATTTctatagAAACAgtAtAG | CCR5wt/hc-2 | 1 | 74848858 | 3 | 45 |
| VEZT | 12 | 18 | 75.0 | 94236444 | R_5_R | CTcTTcCAGTTaagtagggACTGgAAAAG | CCR5wt/hc-1;CCR5wt/hc-3; CCR5wt/n-1;CCR5wt/n-2 | 5 | 94236440-94236472 | 1-29 | 143 |
| ADAMTSL1 | 9 | 17 | 70.8 | 18745601 | R_5_R | CTTTTCAGTTTttagggcAcAgCcAtAt | CCR5wt/hc-1 | 1 | 18745598 | 3 | 47 |
| AGBL1 | 15 | 17 | 70.8 | 84882294 | L_8_L | GTTAaCCTCAgTTagggactgGATGtTgCTGat | CCR5wt/n-1 | 1 | 84882524 | 70 | 48 |
| AKAP13 | 15 | 17 | 70.8 | 83950939 | R_6_R | CTTTTcCggTTTtgctaGActgGGAAGAa | CCR5wt/n-1 | 1 | 83950935 | 4 | 49 |
| ANXA8L2 | 10 | 17 | 70.8 | 47010363 | R_5_L | CTTTTaTAGAGaaattattGATGAGAaTtAC | CCR5wt/n-1 | 1 | 47010351 | 12 | 50 |
| C21orf70 | 21 | 17 | 70.8 | 45269125 | R_6_L | CTTaTcCAGTtTatcatgGATGAGcATTca | CCR5wt/hc-1 | 1 | 45269123 | 2 | 51 |
| C9orf84 | 9 | 17 | 70.8 | 113545977 | R_6_L | CTTTTaCAGTTTgcccaacAAaTGcAgtG | CCR5muF/n-3 | 1 | 113545959 | 18 | 52 |
| CCR2 | 3 | 17 | 70.8 | 46381746 | L_4_L | GTCATCtTatTTtaagaAAAATGCcAcAG | CCR5wt/hc-1 | 1 | 46381717 | 29 | 53 |
| CFHR5 | 1 | 17 | 70.8 | 195222427 | R_8_R | ggTTTcCAGTTTcatccatgAccCTGCAAAgG | CCR5wt/hc-2 | 1 | 19522285 | 142 | 54 |
| CFLAR | 2 | 17 | 70.8 | 201692281 | L_10_L | GTCccCaTaAcCtcacaatgtgtTGAG-GAaGAC | CCR5wt/hc-2 | 1 | 201692282 | 1 | 55 |
| CKS2 | 9 | 17 | 70.8 | 91114563 | R_5_R | CTgTctCAcTTgttcagAAAcCggAAAAG | CCR5wt/hc-1 | 1 | 91114556 | 7 | 56 |

TABLE 2-continued

| RefSeq | ChrMatch | Identify [%] | OS Locus | Configuration | Motif Sequence | Samples | No. Of IS | Region of IS | Distance to Motif | SEQ ID NO |
|---|---|---|---|---|---|---|---|---|---|---|
| CMPK1 | 1 | 17 | 70.8 | 47586318 | R_5_R | acaTTcCAGTTTagatgctaATGCAAAAG | CCR5wt/n-1 | 1 | 47583628 | 11 | 57 |
| CNTN1 | 12 | 17 | 70.8 | 39833854 | R_5_R | CTTTTcacaTTTtaaagtAAgTGaAAAAG | CCR5muF/n-1 | 1 | 39833749 | 105 | 58 |
| CPXR1 | X | 17 | 70.8 | 80089969 | R_10_L | CTTTTaCAGTTcatagaagaagGtTGAGag-TaAg | CCR5muF/n-3 | 1 | 80089969 | 0 | 59 |
| EPHA3 | 3 | 17 | 70.8 | 88818701 | R_6_R | CTTTTGgcaTTaaaaatatAACTtCAAAAa | CCR5muF/n-1 | 1 | 88818701 | 0 | 60 |
| ETNK1 | 12 | 17 | 70.8 | 22675308 | R_5_L | CcaTTaCAGTTTaaaaaGATGAGttacGAa | CCR5wt/hc-2 | 1 | 22675310 | 3 | 61 |
| EXPH5 | 11 | 17 | 70.8 | 107965026 | R_5_R | CTTTTcCAGgcccacaggaGTGCATAAG | CCR5muF/n-3 | 1 | 107965019 | 7 | 62 |
| FBXL11 | 11 | 17 | 70.8 | 66720371 | R_5_L | CTaTTaCAGTTTaagaGATGAGGtctca | CCR5muF/hc-1;CCR5muF/hc-2;CCR5muF/hc-1;CCR5muF/n-3;CCR5wt/hc-1;CCR5wt/hc-2;CCR5wt/hc-3;CCR5wt/hc-4;CCR5wt/n-1;CCR5wt/n-2 | 18 | 66720344-66720389 | 1-27 | 63 |
| GLB1L2 | 11 | 17 | 70.8 | 133712023 | R_3_R | CTTTcCtGTTTatgAtgCTGtcAAtG | CCR5wt/hc-1 | 1 | 133712015 | 8 | 64 |
| HMCN1 | 1 | 17 | 70.8 | 183767378 | R_2_L | CTcTTcCAGTTTatGAgGAaGAGaaGGtg | CCR5muF/n-3 | 1 | 183767381 | 3 | 65 |
| IRF8 | 16 | 17 | 70.8 | 84608111 | L_2_L | GgCcTcagGATCctcAACTGtAAAAt | CCR5wt/hc-1 | 1 | 84608107 | 4 | 66 |
| LPP | 3 | 17 | 70.8 | 189607262 | R_10_R | CTcTggCtGTTTtcttccctttAggCTGCt-gAAG | CCR5wt/hc-2 | 1 | 189607402 | 140 | 67 |
| MKI67 | 10 | 17 | 70.8 | 130093407 | L_8_R | GTgATgCTCcgCagagtcgtAgACaGgAAAAG | CCR5wt/hc-1 | 1 | 130093511 | 104 | 68 |
| MYOM3 | 1 | 17 | 70.8 | 24270059 | L_4_R | ccCgTCCTCATcAcTcactgcAACaGCAAAa | CCR5wt/hc-2 | 1 | 24270061 | 2 | 69 |
| NUP35 | 2 | 17 | 70.8 | 184157972 | R_3_L | CTTTTGCccTTTcagtATGAtatTGgC | CCR5wt/hc-1 | 1 | 184157877 | 95 | 70 |
| OLFM3 | 1 | 17 | 70.8 | 102275277 | R_4_R | aTgTTtCccTTTaagAAAACTGcCAAAt | CCR5wt/hc-1 | 1 | 102275360 | 83 | 71 |
| PLA2G4E | 15 | 17 | 70.8 | 40059400 | L_6_R | ttgATgCTCAgCagtagatAACTGgAAcAG | CCR5muF/n-3 | 1 | 40059399 | 1 | 72 |
| PLCXD3 | 5 | 17 | 70.8 | 41357500 | L_10_R | GTtATCCAaAcCaaaaagacaAAACTG-gAAgAa | CCR5muF/n-1 | 1 | 41357554 | 54 | 73 |
| PPP3CA | 4 | 17 | 70.8 | 102451010 | R_6_R | CTTaTtCAaaTTaaataaAAACTataAAAtg | CCR5wt/hc-1 | 1 | 102451137 | 127 | 74 |
| PSMA1 | 11 | 17 | 70.8 | 14557387 | R_3_L | CTTcTGaAGgTTctaGAaGAGaaATGct | CCR5wt/hc-2 | 1 | 14557380 | 7 | 75 |
| PTPN23 | 3 | 17 | 70.8 | 47393917 | L_5_R | CTgTTcCAGcccatactgAACTGCAAcAG | CCR5wt/hc-1 | 1 | 47393914 | 3 | 76 |
| RPL22 | 1 | 17 | 70.8 | 6168296 | R_5_R | CTTTTGCAtTactgtttgAAtTtCAgAAG | CCR5wt/hc-4 | 1 | 6168223 | 73 | 77 |
| SETD4 | 21 | 17 | 70.8 | 36356367 | R_5_R | CTTTTaCAGTTagatacAACTGccAgc | CCR5wt/hc-1 | 1 | 36356364 | 3 | 78 |
| SH3TC2 | 5 | 17 | 70.8 | 148432638 | R_1_R | tTTTTtCAGTTTgAAtgaGCCAgAgG | CCR5wt/hc-2 | 1 | 148432732 | 95 | 79 |
| SIN3B | 19 | 17 | 70.8 | 16834041 | L_0_L | cTCATtcGCATCcATGAtGtTGAa | CCR5wt/hc-3 | 1 | 16833897 | 144 | 80 |
| SOX9 | 17 | 17 | 70.8 | 67071530 | L_9_L | CaaTTGCAGTTTtaccggctttATGtGaATGga | CCR5wt/hc-2 | 1 | 67071456 | 74 | 81 |
| TBC1D16 | 17 | 17 | 70.8 | 75485496 | R_3_R | gaTTTtCAGTTTggAAAgattAAAAG | CCR5wt/hc-1 | 1 | 75485418 | 78 | 82 |
| ZCCHC14 | 16 | 17 | 70.8 | 86056726 | R_2_L | CTgTTaCAGTTTaaagaGAGgAgGgcC | CCR5muF/hc-1;CCR5wt/hc-1;CCR5muF/hc-2;CCR5wt/hc-4 | 9 | 86056724-86056739 | 2-13 | 83 |
| ZCCHC6 | 9 | 17 | 70.8 | 88240282 | R_5_R | CTTTTcCAcTcTtatgaAgAaGaAAAAG | CCR5wt/hc-2 | 1 | 88240267 | 15 | 84 |
| ZNF254 | 19 | 17 | 70.8 | 24366423 | R_0_R | gcTTTTGCAGccTcTAtAgTGgAAAAG | CCR5muF/n-1 | 1 | 24366557 | 134 | 85 |
| SOS1 | 2 | 16 | 66.7 | 39202364 | R_3_R | CTTTTGCgGTTcttccgACTagAtAt | CCR5wt/hc-2;CCR5wt/n-1 | 3 | 39202367-39202376 | 4-13 | 86 |

TABLE 2-continued

| RefSeq | ChrMatch | Identify [%] | OS Locus | Configuration | Motif Sequence | Samples | No. of IS | Region of IS | Distance to Motif | SEQ ID NO |
|---|---|---|---|---|---|---|---|---|---|---|
| C3orf59 | 3 | 16 | 194006348 | R_5_R | CTTTTcCtaccacacataAAACTGgAAgAG | CCR5wt/hc-1;CCR5wt/hc-2;CCR5wt/hc-2;CCR5wt/hc-4 | 6 | 194006325-194006350 | 3-23 | 87 |
| PTGES2 | 9 | 16 | 129917964 | L_5_L | caCccCCTCATCttacaGATGAGGAacct | CCR5wt/hc-2 | 2 | 129917964-129917966 | 1-3 | 88 |
| PCDH9 | 13 | 16 | 63911404 | R_1_L | tTTaTGCAcTTcatATGAGcATaAg | CCR5wt/hc-2 | 2 | 63911341-63911481 | 63-78 | 89 |
| ACSM5 | 16 | 16 | 20330794 | R_5_R | CccTTcCAGTTgttcatcAACTGaAggAG | CCR5wt/hc-2 | 2 | 20330795-20330805 | 2-12 | 90 |
| UQCRFS1 | 19 | 16 | 30536 | L_5_R | GaCAgaaTCATTcccggAAACTGCgtAG | CCR5wt/hc-3;CCR5wt/n-3 | 2 | 32430290-32430544 | 9-246 | 91 |
| TMEM77 | 1 | 15 | 111427840 | R_7_R | tcTTTGgAGTTTgtaagtttAtaTGCAAtca | CCR5muF/n-1 | 2 | 111427843-111428070 | 4-231 | 92 |
| FCGR1B | 1 | 15 | 121185625 | R_5_R | CTTgTGtTgTgtattcAACTgcAgAG | CCR5muF/hc-1;CCR5muF/hc-2;CCR5muF/n-1 | 3 | 121185586-121185649 | 6-39 | 93 |
| FCGR1B | 1 | 15 | 121186452 | L_5_R | GaCAgaaTCATTcccacAAACTGCgttG | CCR5muF/hc-2;CCR5wt/hc-4 | 2 | 121186486 | | 94 |
| CCR2 | 3 | 15 | 46379384 | R_2_L | tTTTTGttGTTgtTgtGtTtAC | CCR5muF/hc-1;CCR5wt/hc-2 | — | 46379064-46379301 | 83-320 | 95 |
| UQCRFS1 | 19 | 15 | 32423943 | R_5_R | CTTgTGttGTGtgtattcAACTcacAgAG | CCR5muF/n-1 | 2 | 32423939-32423947 | 4-5 | 144 |

(see previous page): Off-target sites in K562 cells treated with ZFN specific for CCR5. Correlation between experimentally identified IS and theoretical off-target loci, that harbor a partial sequence similarity to the CCR5 target site. Preferred IDLV integration sites are underlined in blue.

TABLE 3

| RefSeq | IS ChrMatch | Identity [%] | OS Locus | Configuration | Motif Sequence | Samples | No. of IS | Region of IS | Distance to Motif | SEQ ID NO |
|---|---|---|---|---|---|---|---|---|---|---|
| KIAA0528 | 12 | 87.5 | 22563144 | L_5_L | CTTCCAtAGTtagagACTCTGGcAG | IL2RG2/n-1 | 2 | 22563138-22563144 | 1-6 | 145 |
| SLC36A1 | 5 | 83.3 | 150845074 | L_5_L | CTgCCCCAGAGTatataCACTGGcAG | IL2RG1/hi-1 | 1 | 150845075 | 2 | 96 |
| ANXA5 | 4 | 79.2 | 122733977 | R_5_L | tGcAGCCaCTTTtaaaACTCTtGGcAG | IL2RG2/n-1 | 1 | 122733978 | 2 | 97 |
| A26P1 | 16 | 75.0 | 7985881 | L_5_R | CTgCCACAGRGTgtcaAcAcCaCaCtG | IL2RG2/n-1 | 2 | 7985881-7985892 | 1-12 | 98 |
| CLYBL | 13 | 75.0 | 99364035 | L_6_L | CTTCCtCAGAGggagcaagtgCTGgGGAAG | IL2RG1/hi-1 | 1 | 99364038 | 3 | 99 |
| COL18A1 | 21 | 75.0 | 45651314 | L_5_L | CTgCCCAGccTcaagcACTCTGgGcAG | IL2RG1/hi-2 | 1 | 45651310 | 4 | 100 |
| FAM148B | 15 | 75.0 | 60231561 | L_1_R | CTTCCAtAGAGTagAAtCtGcCCt | IL2RG2/n-1 | 1 | 60231567 | 7 | 101 |
| GK5 | 3 | 75,0 | 143380386 | L_5_R | CTgCCAAtAGTtttcAAAGtGGCTCta | IL2RG2/n-1 | 1 | 143380377 | 9 | 102 |
| LOC391343 | 2 | 75.0 | 868071 | L_2_R | gTTCCtCAGAGTcCTACTCTtTGGAAG | IL2RG2/n-1 | 1 | 868126 | 55 | 103 |
| MGA | 15 | 75.0 | 39782901 | L_0_L | tcTCCAtattGTACTCTtTGGAAG | IL2RG2/n-1 | 1 | 39782912 | 11 | 104 |
| NOMO2 | 16 | 75.0 | 18019661 | R_6_L | tGGGgaCGCTTTtcttgcACTCTTaGaAAG | IL2RG2/n-1 | 1 | 18019580 | 81 | 105 |
| PTCHD2 | 1 | 75.0 | 11456399 | L_5_L | CTgCCtccGAGTactcaACTCgGTGGctG | II2OO1/N-1 | 1 | 11456396 | 3 | 106 |
| RAD51L1 | 14 | 75.0 | 67436348 | L_9_L | CTTtacCAGAGTcactggcTAgTaaGTGGAAG | IL2RG1/hi-1 | 1 | 67436353 | 6 | 107 |
| SLC31A1 | 9 | 75.0 | 115023870 | R_5_L | CctgCCGCTTTcctcagCTCcGcGGAAG | IL2RG1/n-1; IL2RG2/n-1; IL2RG1/hi-3 | 4 | 115023855-115023873 | 4-15 | 108 |
| AP4S1 | 14 | 70.8 | 30623480 | L_5_L | CTTCCAttAGTggaaacCTCTgtgCAG | IL2RG1/hi-1 | 1 | 30623465 | 15 | 109 |
| ARHGEF11 | 1 | 70.8 | 155222666 | R_2_R | tGGAGgCtCTgTcaAAAGgGGCcCTG | IL2RG2/n-1 | 1 | 155222720 | 54 | 110 |
| CENPC1 | 4 | 70.8 | 67948181 | L_9_R | aTTCCACAaAaaagagtgtttcAAAtCtGCTCtG | IL2RG2/n-1 | 1 | 67948221 | 41 | 111 |
| CTTNBP2NL | 1 | 70.8 | 112620146 | L_5_L | CTTCCtCcaAaacagACTCTaaGGAAG | IL2RG2/n-1 | 1 | 112620143 | 3 | 112 |
| DTWD2 | 5 | 70.8 | 117894727 | L_7_L | CTTtgAacaAGTttttaaACTCTGTtGAAc | IL2RG1/hi-1 | 1 | 117894800 | 74 | 113 |
| EPHA7 | 6 | 70.8 | 94185716 | L_4_R | CcTCCcctGtGTgtgcAAAGcGagCaG | IL2RG1/hi-1 | 1 | 94185716 | 0 | 114 |
| FAM19A1 | 3 | 70.8 | 68258713 | R_8_R | CatAcCCGCTTTcaatacacAAAGtGaTCtG | IL2RG2/n-1 | 1 | 68258581 | 132 | 115 |
| FBXL2 | 3 | 70.8 | 33287060 | L_6_L | CTTCCAGGaTctgtgACTCTtTCgGtc | IL2RG1/hi-2 | 1 | 33286929 | 131 | 116 |
| HINT1 | 5 | 70.8 | 130386967 | L_5_L | CTgCCtaAGAGTtagcctgCTcTGGAAG | IL2RG2/n-1 | 1 | 130386962 | 5 | 117 |
| HLCS | 21 | 70.8 | 37233561 | R_5_R | tGGAcCCGCTTTctcaAgtgtGgTCcG | IL2RG1/n-1 | 1 | 37233552 | 9 | 118 |
| HS6ST3 | 13 | 70.8 | 95977842 | R_4_R | CaGAGCCtCTTgtagataAGtGGgTCaG | IL2RG2/n-1 | 1 | 95977843 | 1 | 119 |
| IFIT1 | 10 | 70.8 | 91142862 | L_1_R | tACCACAGAgaAAAGcAGaCCc | IL2RG2/n-1 | 1 | 91142790 | 72 | 120 |
| KCTD8 | 4 | 70.8 | 43587881 | L_5_R | gTTCCAgAcAGTggaatgAtGgGGCTCaG | IL2RG1/hi-3 | 2 | 43587975-43587976 | 95-96 | 121 |
| KIAA0355 | 19 | 70.8 | 39530643 | L_6_L | CagaccCAGAGTtgcacgCTaTGTGGcAG | IL2RG1/hi-3 | 1 | 39530645 | 2 | 122 |
| KSP37 | 10 | 70,8 | 44637462 | R_0_L | CaGAGCCCCTgcACTCaGaGGcAG | IL2RG2/n-1 | 1 | 44637467 | 5 | 123 |
| MBTD1 | 17 | 70.8 | 46692505 | L_1_L | CTTCcACgCTgAAGcCTCTgCAgG | IL2RG2/n-1 | 1 | 46692491 | 14 | 124 |
| NEB | 2 | 70.8 | 152083108 | R_5_R | tGtgGCCtCTTTtaggtgAAgCtGCTCCa | IL2RG2/n-1 | 1 | 152083177 | 70 | 125 |
| OSBPL7 | 17 | 70.8 | 43244823 | R_5_L | CaGAGCCtCCTgccatctcCTtgGTGGAAG | IL2RG1/hi-2 | 1 | 43244819 | 4 | 126 |
| PCBD1 | 10 | 70.8 | 72329416 | R_6_L | CGtAtCCaGTTTcctatccCTtgGTGGAAG | IL2RG2/n-1 | 1 | 72329412 | 4 | 127 |
| RAD9A | 11 | 70.8 | 66922162 | R_3_R | CGGtGCCGagactcccAAGcGGCTCtG | IL2RG1/hi-2 | 1 | 66922162 | 5 | 128 |
| RRAS2 | 11 | 70.8 | 14273926 | L_0_L | CTatCACAcACTgCTtTGTgtAAG | IL2RG1/n-1 | 1 | 14273892 | 34 | 129 |
| RRS1 | 8 | 70.8 | 67452086 | R_4_L | gaGcGCCCcagTcactgCTCTGTGGAAG | IL2RG1/n-1 | 2 | 67452069-67452074 | 12-17 | 130 |

TABLE 3-continued

| RefSeq | IS ChrMatch | IS Identity [%] | OS Locus | Configuration | Motif Sequence | Samples | No. of IS | Region of IS | Distance to Motif | SEQ ID NO |
|---|---|---|---|---|---|---|---|---|---|---|
| SCARB1 | 12 | 70.8 | 123822430 | L_5_R | CTTCCcCAGttTaaaatcAAtCcaCTCCG | IL2RG1/n-1 | 3 | 123822426-123822444 | 3-15 | 131 |
| SEC16A | 9 | 70.8 | 138461130 | R_6_L | CGtAcCCGCTcacctgggCTCTGgGcAG | IL2RG1/hi-1;IL2RG1/n-1; IL2RG2/n-1 | 4 | 138461051-138461132 | 1-79 | 132 |
| SF3B1 | 2 | 70.8 | 197957062 | R_5_R | CtGAGCatCTTTgaactAAttCaGCTCtg | IL2RG2/n-1 | 4 | 197956936-197957142 | 8-126 | 133 |
| SHROOM1 | 5 | 70.8 | 132193625 | R_10_L | CaGAcCCGgTTacctgggt-tcAaTCTcTGGgAG | IL2RG1/hi-3 | 1 | 132193763 | 138 | 134 |
| STAG1 | 3 | 70.8 | 137593393 | L_5_L | CTgCccCAGAGCttccaACTCTGgGaAtc | IL2RG1/hi-3;IL2RG1/n-1 | 4 | 137593389-137593400 | 4-8 | 135 |
| SYNE2 | 14 | 70.8 | 63546096 | L_6_R | aTctgcCAGAGTtatgttAAAGgGGCTCtG | IL2RG1/n-1 | 1 | 63546094 | 2 | 136 |
| TOX2 | 20 | 70.8 | 42143811 | R_8_L | aGGgtCCcCTcTcccacggccCTCTGgGGAAG | IL2RG1/n-1 | 1 | 42143939 | 128 | 137 |
| TRIB1 | 8 | 70.8 | 126780005 | R_5_L | CaaAGCCtgTcaaaatACTCTGTGGcAG | IL2RG2/n-1 | 1 | 126779996 | 9 | 138 |
| ZNF280D | 15 | 70.8 | 54881712 | L_5_R | CTgCCcttGAGTtttatAAAGgGGCTatG | IL2RG2/n-1 | 1 | 54881705 | 7 | 139 | off-target sites in K562 cells treated with IL2RG targeting ZFN. Correlation between experimentally identified IS and theoretical off-target loci, that harbor a partial sequence similarity to the IL2RG target site. Preferred IDLV integration sites are underlined in red.

The invention claimed is:

1. A method for determining the in vivo distribution of double-strand breaks induced by an endonuclease in a host cell, comprising:
   a) incubating the host cell and a linear polynucleotide comprising a known sequence and encoding the endonuclease, wherein the linear polynucleotide comprising the known sequence and encoding the endonuclease is integrated into double-strand breaks in the genome in a sequence independent manner by non-homologous end joining;
   b) detecting at least 50 in vivo insertion sites of the linear polynucleotide in the genome of the host cell by (i) amplifying polynucleotides from the genome using primers priming in the linear polynucleotide comprising the known sequence and (ii) determining at least one nucleic acid sequence which is in the genome and adjacent to the linear polynucleotide comprising the known sequence;
   c) determining the in vivo positions of double-strand breaks based on the sequence information obtained in step b); and
   d) determining the in vivo distribution of double-strand breaks induced by the endonuclease in the host cell.

2. The method of claim 1, wherein the linear polynucleotide is an integrase-deficient lentivirus.

3. The method of claim 1, wherein double-strand breaks are induced by a zinc-finger nuclease.

4. The method of claim 1, wherein the linear polynucleotide comprises an integrase-deficient lentivirus and encodes the zinc-finger nuclease.

5. The method of claim 1, wherein the insertion sites are detected by a method comprising PCR amplification followed by DNA sequencing.

6. The method of claim 5, wherein the PCR is LAM-PCR.

7. A method for determining the in vivo specificity of an endonuclease, comprising:
   a) incubating a host cell comprising the endonuclease and a linear polynucleotide comprising a known sequence, wherein the linear polynucleotide comprising the known sequence is integrated into double-strand breaks in the genome in a sequence independent manner by non-homologous end joining;
   b) detecting at least 50 in vivo insertion sites of the linear polynucleotide in the genome of the host cell by (i) amplifying polynucleotides from the genome using primers priming in the linear poiynucieotide comprising the known sequence and (ii) determining at least one nucleic acid sequence which is in the genome and adjacent to the linear polynucleotide comprising the known sequence;
   c) determining the in vivo recognition sites of the endonuclease based on the sequence information obtained in step b); and
   d) assessing the in vivo specificity of the endonuclease.

8. The method of claim 7, wherein the endonuclease is a Zinc-finger endonuclease.

9. The method of claim 7, wherein the linear polynucleotide is an integrase-deficient lentivirus.

10. The method of claim 7, wherein the insertion sites are detected by a method comprising PCR amplification followed by DNA sequencing.

11. The method of claim 10, wherein the PCR is LAM-PCR.

12. A method for obtaining an endonuclease with an altered in vivo specificity, comprising:
   a) providing at least one mutant of an endonuclease with a known recognition sequence;
   b) determining the in vivo specificity of the mutant of an endonuclease by a method comprising:
      i) incubating a host cell comprising the endonuclease and a linear polynucleotide comprising a known sequence, wherein the linear polynucleotide comprising the known sequence is integrated into double-strand breaks in the genome in a sequence independent manner by non-homologous end joining;

ii) detecting at least 50 in vivo insertion sites of the linear polynucleotide in the genome of the host cell by (aa) amplifying polynucleotides from the genome using primers priming in the linear polynucleotide comprising the known sequence and (bb) determining at least one nucleic acid sequence which is in the genome and adjacent to the linear polynucleotide comprising the known sequence;

iii) determining the in vivo recognition sites of the endonuclease based on the sequence information obtained in step ii); and iv) assessing the in vivo specificity of the endonuclease;

c) comparing the recognition sites recognized by the at least one mutant endonuclease with the recognition sites recognized by the unmodified endonuclease; and d) obtaining an endonuclease with an altered in vivo specificity.

13. The method of claim 12, wherein the altered in vivo specificity is an increased in vivo specificity for a specific recognition sequence.

14. The method of claim 12, wherein the endonuclease is a Zinc-finger endonuclease.

15. The method of claim 1, wherein the determined position of the in vivo localization of double-strand breaks is within 5000 nucleotides from the position of double-strand breaks.

* * * * *

SEQUENCE LISTING

<160> NUMBER OF SEQ ID NOS: 145

<210> SEQ ID NO 1
<211> LENGTH: 29
<212> TYPE: DNA
<213> ORGANISM: Homo sapiens

<400> SEQUENCE: 1
gtcatcctca tcctgataaa ctgcaaaag                                   29

<210> SEQ ID NO 2
<211> LENGTH: 29
<212> TYPE: DNA
<213> ORGANISM: Homo sapiens

<400> SEQUENCE: 2
gtcatcctca tctcacggat gaggatgcc                                   29

<210> SEQ ID NO 3
<211> LENGTH: 30
<212> TYPE: DNA
<213> ORGANISM: Homo sapiens

<400> SEQUENCE: 3
gttttgcagt ttcacctcaa actgcaaaag                                  30

<210> SEQ ID NO 4
<211> LENGTH: 29
<212> TYPE: DNA
<213> ORGANISM: Homo sapiens

<400> SEQUENCE: 4
gtcgtcctca tcttaataaa ctgcaaaaa                                   29

<210> SEQ ID NO 5
<211> LENGTH: 30
<212> TYPE: DNA
<213> ORGANISM: Homo sapiens

<400> SEQUENCE: 5
gttttgctgt ttcagcttaa actgcaaaag                                  30

<210> SEQ ID NO 6
<211> LENGTH: 30
<212> TYPE: DNA
<213> ORGANISM: Homo sapiens

<400> SEQUENCE: 6
gttttgctgt ttcacctaaa actgcaaaag                                  30

<210> SEQ ID NO 7
<211> LENGTH: 30
<212> TYPE: DNA
<213> ORGANISM: Homo sapiens

<400> SEQUENCE: 7
cttttgctgt tgcacctcaa actgcaaaag                                  30

<210> SEQ ID NO 8
<211> LENGTH: 32
<212> TYPE: DNA
<213> ORGANISM: Homo sapiens

<400> SEQUENCE: 8

-continued

```
attttgcagt tttgtcattc aaactgcaaa tg                                32
```

<210> SEQ ID NO 9
<211> LENGTH: 31
<212> TYPE: DNA
<213> ORGANISM: Homo sapiens

<400> SEQUENCE: 9

```
gtcatcccca tcagggtaca atctgcaaaa g                                 31
```

<210> SEQ ID NO 10
<211> LENGTH: 29
<212> TYPE: DNA
<213> ORGANISM: Homo sapiens

<400> SEQUENCE: 10

```
cttccacaga gtgggttaaa gcggctccg                                    29
```

<210> SEQ ID NO 11
<211> LENGTH: 28
<212> TYPE: DNA
<213> ORGANISM: Homo sapiens

<400> SEQUENCE: 11

```
cttccacaga gtgcctactc tgtgtcag                                     28
```

<210> SEQ ID NO 12
<211> LENGTH: 32
<212> TYPE: DNA
<213> ORGANISM: Homo sapiens

<400> SEQUENCE: 12

```
cttccacaga gtcatttccc gctcttcgga ag                                32
```

<210> SEQ ID NO 13
<211> LENGTH: 32
<212> TYPE: DNA
<213> ORGANISM: Homo sapiens

<400> SEQUENCE: 13

```
cttctacaga gccggcgtac actctgtgga tg                                32
```

<210> SEQ ID NO 14
<211> LENGTH: 32
<212> TYPE: DNA
<213> ORGANISM: Homo sapiens

<400> SEQUENCE: 14

```
cttcctccga gtccaggtgg actctgtgga tg                                32
```

<210> SEQ ID NO 15
<211> LENGTH: 32
<212> TYPE: DNA
<213> ORGANISM: Homo sapiens

<400> SEQUENCE: 15

```
cttccacaga gttttcaaac actaggtgga cg                                32
```

<210> SEQ ID NO 16
<211> LENGTH: 31
<212> TYPE: DNA
<213> ORGANISM: Homo sapiens

<400> SEQUENCE: 16
cttccagaga gcaaccccca ctctttggaa g                           31

<210> SEQ ID NO 17
<211> LENGTH: 32
<212> TYPE: DNA
<213> ORGANISM: Homo sapiens

<400> SEQUENCE: 17
cagccagaga gtcactggtc actctgtgga ag                          32

<210> SEQ ID NO 18
<211> LENGTH: 30
<212> TYPE: DNA
<213> ORGANISM: Homo sapiens

<400> SEQUENCE: 18
cttccactgt gtcctagaac tctgtgcaag                             30

<210> SEQ ID NO 19
<211> LENGTH: 31
<212> TYPE: DNA
<213> ORGANISM: Homo sapiens

<400> SEQUENCE: 19
cttccacaga gaaattccga ctctctggaa a                           31

<210> SEQ ID NO 20
<211> LENGTH: 29
<212> TYPE: DNA
<213> ORGANISM: Homo sapiens

<400> SEQUENCE: 20
cttccacaca gtggtattct ctatggaag                              29

<210> SEQ ID NO 21
<211> LENGTH: 29
<212> TYPE: DNA
<213> ORGANISM: Homo sapiens

<400> SEQUENCE: 21
cttccatata gttagagact ctgtggcag                              29

<210> SEQ ID NO 22
<211> LENGTH: 28
<212> TYPE: DNA
<213> ORGANISM: Homo sapiens

<400> SEQUENCE: 22
cttccacagg gtgcctactc tgtgtcag                               28

<210> SEQ ID NO 23
<211> LENGTH: 29
<212> TYPE: DNA
<213> ORGANISM: Homo sapiens

<400> SEQUENCE: 23
atcatcctca tcttgcagat gagggagac                              29

<210> SEQ ID NO 24
<211> LENGTH: 30
<212> TYPE: DNA
<213> ORGANISM: Homo sapiens -continued

<400> SEQUENCE: 24
gtcatcctca tcttcatcca tgaggaagag                                              30

<210> SEQ ID NO 25
<211> LENGTH: 29
<212> TYPE: DNA
<213> ORGANISM: Homo sapiens

<400> SEQUENCE: 25
cttttgcatt tcaaataaa caggaaaag                                                29

<210> SEQ ID NO 26
<211> LENGTH: 29
<212> TYPE: DNA
<213> ORGANISM: Homo sapiens

<400> SEQUENCE: 26
catttccagt ttaaagagat gaggaggcc                                               29

<210> SEQ ID NO 27
<211> LENGTH: 29
<212> TYPE: DNA
<213> ORGANISM: Homo sapiens

<400> SEQUENCE: 27
ctgttacagt tcacgagaaa ctgcaagag                                               29

<210> SEQ ID NO 28
<211> LENGTH: 27
<212> TYPE: DNA
<213> ORGANISM: Homo sapiens

<400> SEQUENCE: 28 cttttcagt ttcccaaact gaaactc                                                  27

<210> SEQ ID NO 29
<211> LENGTH: 29
<212> TYPE: DNA
<213> ORGANISM: Homo sapiens

<400> SEQUENCE: 29
cttttgcagt ttctgtgggt gaggactttt                                              29

<210> SEQ ID NO 30
<211> LENGTH: 27
<212> TYPE: DNA
<213> ORGANISM: Homo sapiens

<400> SEQUENCE: 30
cttttgcagt ttatgaagct gcattct                                                 27

<210> SEQ ID NO 31
<211> LENGTH: 29
<212> TYPE: DNA
<213> ORGANISM: Homo sapiens

<400> SEQUENCE: 31
gtagtcctcc tcctgctaaa ctgcaatgg                                               29

<210> SEQ ID NO 32
<211> LENGTH: 26
<212> TYPE: DNA

<210> SEQ ID NO 32
<211> LENGTH: 26
<212> TYPE: DNA
<213> ORGANISM: Homo sapiens

<400> SEQUENCE: 32
catctcatca tcatgatgag gatgac                                          26

<210> SEQ ID NO 33
<211> LENGTH: 29
<212> TYPE: DNA
<213> ORGANISM: Homo sapiens

<400> SEQUENCE: 33
cttttgcagt ttagacaaaa ctgcccggc                                       29

<210> SEQ ID NO 34
<211> LENGTH: 34
<212> TYPE: DNA
<213> ORGANISM: Homo sapiens

<400> SEQUENCE: 34
cttttgcggt ttatacacaa ctgatcagca ttag                                 34

<210> SEQ ID NO 35
<211> LENGTH: 29
<212> TYPE: DNA
<213> ORGANISM: Homo sapiens

<400> SEQUENCE: 35
aatttcctca tctgaaagac gaggatgac                                       29

<210> SEQ ID NO 36
<211> LENGTH: 34
<212> TYPE: DNA
<213> ORGANISM: Homo sapiens

<400> SEQUENCE: 36
cttttacagt ttacaccaaa ccagaatcaa aaac                                 34

<210> SEQ ID NO 37
<211> LENGTH: 28
<212> TYPE: DNA
<213> ORGANISM: Homo sapiens

<400> SEQUENCE: 37 cttttttcagt taattcatct tggaaaag                                       28

<210> SEQ ID NO 38
<211> LENGTH: 28
<212> TYPE: DNA
<213> ORGANISM: Homo sapiens

<400> SEQUENCE: 38
attttgcagt atggaaaatg actatgcc                                        28

<210> SEQ ID NO 39
<211> LENGTH: 24
<212> TYPE: DNA
<213> ORGANISM: Homo sapiens

<400> SEQUENCE: 39
cctttggtct ttgatgatgg tgac                                            24

<210> SEQ ID NO 40
<211> LENGTH: 24

<212> TYPE: DNA
<213> ORGANISM: Homo sapiens

<400> SEQUENCE: 40
ctcctcctca tggaggagga gggc                                    24

<210> SEQ ID NO 41
<211> LENGTH: 29
<212> TYPE: DNA
<213> ORGANISM: Homo sapiens

<400> SEQUENCE: 41
gttatcacca tcccaataaa ctgcacatt                               29

<210> SEQ ID NO 42
<211> LENGTH: 27
<212> TYPE: DNA
<213> ORGANISM: Homo sapiens

<400> SEQUENCE: 42
cgtttgcact ttgtaacaca gcacagg                                 27

<210> SEQ ID NO 43
<211> LENGTH: 31
<212> TYPE: DNA
<213> ORGANISM: Homo sapiens

<400> SEQUENCE: 43
gtttatcatt tctttatata aactgtaaaa g                            31

<210> SEQ ID NO 44
<211> LENGTH: 30
<212> TYPE: DNA
<213> ORGANISM: Homo sapiens

<400> SEQUENCE: 44
cacttccagt ttattatgaa accgtgaaag                              30

<210> SEQ ID NO 45
<211> LENGTH: 29
<212> TYPE: DNA
<213> ORGANISM: Homo sapiens

<400> SEQUENCE: 45
cttttacatt tctatagaaa cagtaatag                               29

<210> SEQ ID NO 46
<211> LENGTH: 28
<212> TYPE: DNA
<213> ORGANISM: Homo sapiens

<400> SEQUENCE: 46
tctttcagtt aagtagggac tggaaaag                                28

<210> SEQ ID NO 47
<211> LENGTH: 29
<212> TYPE: DNA
<213> ORGANISM: Homo sapiens

<400> SEQUENCE: 47 cttttttcagt ttttagggca cagccatat                              29

<210> SEQ ID NO 48

```
<211> LENGTH: 32
<212> TYPE: DNA
<213> ORGANISM: Homo sapiens

<400> SEQUENCE: 48
gttaacctca gctaggactg gatgttgctg at                              32

<210> SEQ ID NO 49
<211> LENGTH: 30
<212> TYPE: DNA
<213> ORGANISM: Homo sapiens

<400> SEQUENCE: 49
cttttccggt tttgcctaga ctgggaagaa                                 30

<210> SEQ ID NO 50
<211> LENGTH: 29
<212> TYPE: DNA
<213> ORGANISM: Homo sapiens

<400> SEQUENCE: 50
cttttataga aattattgat gagaattac                                  29

<210> SEQ ID NO 51
<211> LENGTH: 30
<212> TYPE: DNA
<213> ORGANISM: Homo sapiens

<400> SEQUENCE: 51
cttatccagt ctatcatgga tgagcattca                                 30

<210> SEQ ID NO 52
<211> LENGTH: 29
<212> TYPE: DNA
<213> ORGANISM: Homo sapiens

<400> SEQUENCE: 52
cttttacagt tgccaaacaa atggaagtg                                  29

<210> SEQ ID NO 53
<211> LENGTH: 28
<212> TYPE: DNA
<213> ORGANISM: Homo sapiens

<400> SEQUENCE: 53
gtcatcttat tttaagaaat tgccacag                                   28

<210> SEQ ID NO 54
<211> LENGTH: 32
<212> TYPE: DNA
<213> ORGANISM: Homo sapiens

<400> SEQUENCE: 54
ggtttccagg ttcatccatg accctgcaaa gg                              32

<210> SEQ ID NO 55
<211> LENGTH: 34
<212> TYPE: DNA
<213> ORGANISM: Homo sapiens

<400> SEQUENCE: 55
gtccccataa cctcacaatg tggttgagga agac                            34
```

```
<210> SEQ ID NO 56
<211> LENGTH: 29
<212> TYPE: DNA
<213> ORGANISM: Homo sapiens

<400> SEQUENCE: 56
ctgtctcact tgttcagaaa ccggaaaag                              29

<210> SEQ ID NO 57
<211> LENGTH: 29
<212> TYPE: DNA
<213> ORGANISM: Homo sapiens

<400> SEQUENCE: 57
acattccagt ttagatgcta atgcaaaag                              29

<210> SEQ ID NO 58
<211> LENGTH: 29
<212> TYPE: DNA
<213> ORGANISM: Homo sapiens

<400> SEQUENCE: 58
cttttcacat tttaaagtaa gtgaaaaag                              29

<210> SEQ ID NO 59
<211> LENGTH: 34
<212> TYPE: DNA
<213> ORGANISM: Homo sapiens

<400> SEQUENCE: 59
cttttacagt tcatagagaa gagttgagag taag                        34

<210> SEQ ID NO 60
<211> LENGTH: 30
<212> TYPE: DNA
<213> ORGANISM: Homo sapiens

<400> SEQUENCE: 60
cttttggcat taaaatata acttcaaaaa                              30

<210> SEQ ID NO 61
<211> LENGTH: 29
<212> TYPE: DNA
<213> ORGANISM: Homo sapiens

<400> SEQUENCE: 61
ccattacagt ttaaaaagat gagttagaa                              29

<210> SEQ ID NO 62
<211> LENGTH: 29
<212> TYPE: DNA
<213> ORGANISM: Homo sapiens

<400> SEQUENCE: 62
cttttccagg ccacacagga ctgcataag                              29

<210> SEQ ID NO 63
<211> LENGTH: 29
<212> TYPE: DNA
<213> ORGANISM: Homo sapiens

<400> SEQUENCE: 63
ctattacagt tttaagagat gaggtctca                              29
```

<210> SEQ ID NO 64
<211> LENGTH: 27
<212> TYPE: DNA
<213> ORGANISM: Homo sapiens

<400> SEQUENCE: 64
cttttcctgt ttatgatgct gtcaatg								27

<210> SEQ ID NO 65
<211> LENGTH: 26
<212> TYPE: DNA
<213> ORGANISM: Homo sapiens

<400> SEQUENCE: 65
ctcttccagt ttatgaggaa gaggtg								26

<210> SEQ ID NO 66
<211> LENGTH: 26
<212> TYPE: DNA
<213> ORGANISM: Homo sapiens

<400> SEQUENCE: 66
ggcctcagca tcctcaactg taaaat								26

<210> SEQ ID NO 67
<211> LENGTH: 34
<212> TYPE: DNA
<213> ORGANISM: Homo sapiens

<400> SEQUENCE: 67
ctctggctgt ttttcttccc ttaggctgct gaag							34

<210> SEQ ID NO 68
<211> LENGTH: 32
<212> TYPE: DNA
<213> ORGANISM: Homo sapiens

<400> SEQUENCE: 68
gtgatgctcc gcagagtcgt agacaggaaa ag							32

<210> SEQ ID NO 69
<211> LENGTH: 27
<212> TYPE: DNA
<213> ORGANISM: Homo sapiens

<400> SEQUENCE: 69
cccgtcctca tcactgcaac agcaaaa								27

<210> SEQ ID NO 70
<211> LENGTH: 27
<212> TYPE: DNA
<213> ORGANISM: Homo sapiens

<400> SEQUENCE: 70
cttttgccct ttcagtatga tattggc								27

<210> SEQ ID NO 71
<211> LENGTH: 28
<212> TYPE: DNA
<213> ORGANISM: Homo sapiens

<400> SEQUENCE: 71
atgtttccct tttaagaaac tgccaaat								28

<210> SEQ ID NO 72
<211> LENGTH: 30
<212> TYPE: DNA
<213> ORGANISM: Homo sapiens

<400> SEQUENCE: 72
ttgatgctca gcagtagata actggaacag                                           30

<210> SEQ ID NO 73
<211> LENGTH: 34
<212> TYPE: DNA
<213> ORGANISM: Homo sapiens

<400> SEQUENCE: 73
gttatccaaa ccaaaaagaa caaaactgga agaa                                       34

<210> SEQ ID NO 74
<211> LENGTH: 30
<212> TYPE: DNA
<213> ORGANISM: Homo sapiens

<400> SEQUENCE: 74
cttattcaaa ttaaataaaa actataaatg                                           30

<210> SEQ ID NO 75
<211> LENGTH: 27
<212> TYPE: DNA
<213> ORGANISM: Homo sapiens

<400> SEQUENCE: 75
cttctgaagg ttctagaaga gaatgct                                              27

<210> SEQ ID NO 76
<211> LENGTH: 29
<212> TYPE: DNA
<213> ORGANISM: Homo sapiens

<400> SEQUENCE: 76
ctgttccagc ccatactgaa ctgcaacag                                            29

<210> SEQ ID NO 77
<211> LENGTH: 29
<212> TYPE: DNA
<213> ORGANISM: Homo sapiens

<400> SEQUENCE: 77
cttttgcatt actgtttgaa tttcagaag                                            29

<210> SEQ ID NO 78
<211> LENGTH: 29
<212> TYPE: DNA
<213> ORGANISM: Homo sapiens

<400> SEQUENCE: 78
cttttacagt ttagatacaa ctggccagc                                            29

<210> SEQ ID NO 79
<211> LENGTH: 25
<212> TYPE: DNA
<213> ORGANISM: Homo sapiens

<400> SEQUENCE: 79
ttttttcagt ttgaatgagc agagg         25

<210> SEQ ID NO 80
<211> LENGTH: 24
<212> TYPE: DNA
<213> ORGANISM: Homo sapiens

<400> SEQUENCE: 80
ctcattcgca tccatgatgt tgaa          24

<210> SEQ ID NO 81
<211> LENGTH: 33
<212> TYPE: DNA
<213> ORGANISM: Homo sapiens

<400> SEQUENCE: 81
caattgcagt tttaccggct ttatgtgaat gga     33

<210> SEQ ID NO 82
<211> LENGTH: 27
<212> TYPE: DNA
<213> ORGANISM: Homo sapiens

<400> SEQUENCE: 82
gattttcagt tttggaaaga ttaaaag         27

<210> SEQ ID NO 83
<211> LENGTH: 26
<212> TYPE: DNA
<213> ORGANISM: Homo sapiens

<400> SEQUENCE: 83
ctgttacagt ttaaagagag gaggcc          26

<210> SEQ ID NO 84
<211> LENGTH: 29
<212> TYPE: DNA
<213> ORGANISM: Homo sapiens

<400> SEQUENCE: 84
cttttccact cttatgaaga aagaaaaag       29

<210> SEQ ID NO 85
<211> LENGTH: 24
<212> TYPE: DNA
<213> ORGANISM: Homo sapiens

<400> SEQUENCE: 85
gctttgcagc ctatagtgga aaag            24

<210> SEQ ID NO 86
<211> LENGTH: 27
<212> TYPE: DNA
<213> ORGANISM: Homo sapiens

<400> SEQUENCE: 86
cttttgcggt tctttcgact agataat         27

<210> SEQ ID NO 87
<211> LENGTH: 29
<212> TYPE: DNA
<213> ORGANISM: Homo sapiens

<400> SEQUENCE: 87
cttttcctac cacacataaa ctggaagag                                29

<210> SEQ ID NO 88
<211> LENGTH: 29
<212> TYPE: DNA
<213> ORGANISM: Homo sapiens

<400> SEQUENCE: 88 cacccctca tcttacagat gaggaacct                                 29

<210> SEQ ID NO 89
<211> LENGTH: 25
<212> TYPE: DNA
<213> ORGANISM: Homo sapiens

<400> SEQUENCE: 89
tttatgcact tcatatgagc ataag                                    25

<210> SEQ ID NO 90
<211> LENGTH: 29
<212> TYPE: DNA
<213> ORGANISM: Homo sapiens

<400> SEQUENCE: 90
cccttccagt tgttcatcaa ctgaaggag                                29

<210> SEQ ID NO 91
<211> LENGTH: 28
<212> TYPE: DNA
<213> ORGANISM: Homo sapiens

<400> SEQUENCE: 91
gacagaatca ttcccggaaa ctgcgtag                                 28

<210> SEQ ID NO 92
<211> LENGTH: 31
<212> TYPE: DNA
<213> ORGANISM: Homo sapiens

<400> SEQUENCE: 92
tctttggagt ttgtaagttt atatgcaatc a                             31

<210> SEQ ID NO 93
<211> LENGTH: 29
<212> TYPE: DNA
<213> ORGANISM: Homo sapiens

<400> SEQUENCE: 93
cttgtgttgt gtgtattcaa ctcacagag                                29

<210> SEQ ID NO 94
<211> LENGTH: 28
<212> TYPE: DNA
<213> ORGANISM: Homo sapiens

<400> SEQUENCE: 94
gacagaatca ttcccacaaa ctgcgttg                                 28

<210> SEQ ID NO 95
<211> LENGTH: 26
<212> TYPE: DNA
<213> ORGANISM: Homo sapiens

```
<400> SEQUENCE: 95
tttttgttgt tgttgttgtt gtttac                                    26

<210> SEQ ID NO 96
<211> LENGTH: 29
<212> TYPE: DNA
<213> ORGANISM: Homo sapiens

<400> SEQUENCE: 96
ctgccccaga gtatataaca ctgtggcag                                 29

<210> SEQ ID NO 97
<211> LENGTH: 29
<212> TYPE: DNA
<213> ORGANISM: Homo sapiens

<400> SEQUENCE: 97
tgcagccact ttttaaaact ctttggcag                                 29

<210> SEQ ID NO 98
<211> LENGTH: 29
<212> TYPE: DNA
<213> ORGANISM: Homo sapiens

<400> SEQUENCE: 98
ctgccacaga gtgctcaaca ccgacactg                                 29

<210> SEQ ID NO 99
<211> LENGTH: 30
<212> TYPE: DNA
<213> ORGANISM: Homo sapiens

<400> SEQUENCE: 99
cttcctcaga gggagcaagt gctggggaag                                30

<210> SEQ ID NO 100
<211> LENGTH: 29
<212> TYPE: DNA
<213> ORGANISM: Homo sapiens

<400> SEQUENCE: 100
ctgccccagc ctcaagcact ctggggcag                                 29

<210> SEQ ID NO 101
<211> LENGTH: 25
<212> TYPE: DNA
<213> ORGANISM: Homo sapiens

<400> SEQUENCE: 101
cttccataga gtagaatctg cccct                                     25

<210> SEQ ID NO 102
<211> LENGTH: 29
<212> TYPE: DNA
<213> ORGANISM: Homo sapiens

<400> SEQUENCE: 102
ctgccaaata gttttttcaaa gtggctcta                                29

<210> SEQ ID NO 103
<211> LENGTH: 26
<212> TYPE: DNA
<213> ORGANISM: Homo sapiens
```

-continued

<400> SEQUENCE: 103
gttcctcaga gtcctaaggg gctcaa                                         26

<210> SEQ ID NO 104
<211> LENGTH: 24
<212> TYPE: DNA
<213> ORGANISM: Homo sapiens

<400> SEQUENCE: 104
tctccatatt gtactctttg gaag                                           24

<210> SEQ ID NO 105
<211> LENGTH: 30
<212> TYPE: DNA
<213> ORGANISM: Homo sapiens

<400> SEQUENCE: 105
tggggacgct ttctttgcac tcttagaaag                                     30

<210> SEQ ID NO 106
<211> LENGTH: 29
<212> TYPE: DNA
<213> ORGANISM: Homo sapiens

<400> SEQUENCE: 106
ctgcctccga gtactcaact cggtggctg                                      29

<210> SEQ ID NO 107
<211> LENGTH: 33
<212> TYPE: DNA
<213> ORGANISM: Homo sapiens

<400> SEQUENCE: 107
ctttaccaga gtcacttggc tagtaagtgg aag                                 33

<210> SEQ ID NO 108
<211> LENGTH: 29
<212> TYPE: DNA
<213> ORGANISM: Homo sapiens

<400> SEQUENCE: 108
cctcgccgct ttcctcagct ccgcggaag                                      29

<210> SEQ ID NO 109
<211> LENGTH: 29
<212> TYPE: DNA
<213> ORGANISM: Homo sapiens

<400> SEQUENCE: 109
cttccattta gtggaaacct ctggtgcag                                      29

<210> SEQ ID NO 110
<211> LENGTH: 26
<212> TYPE: DNA
<213> ORGANISM: Homo sapiens

<400> SEQUENCE: 110
tggaggctct gtcaaaaggg gccctg                                         26

<210> SEQ ID NO 111
<211> LENGTH: 33
<212> TYPE: DNA

```
<213> ORGANISM: Homo sapiens

<400> SEQUENCE: 111
attccacaaa aagagtgttt caaatctgct ctg                              33

<210> SEQ ID NO 112
<211> LENGTH: 29
<212> TYPE: DNA
<213> ORGANISM: Homo sapiens

<400> SEQUENCE: 112
cttcctccaa aacacagact ctaaggaag                                   29

<210> SEQ ID NO 113
<211> LENGTH: 31
<212> TYPE: DNA
<213> ORGANISM: Homo sapiens

<400> SEQUENCE: 113
ctttgaacaa gtttttaaa ctctgttgaa c                                 31

<210> SEQ ID NO 114
<211> LENGTH: 28
<212> TYPE: DNA
<213> ORGANISM: Homo sapiens

<400> SEQUENCE: 114
cctcccctgt gtgtgcaaag cggagcag                                    28

<210> SEQ ID NO 115
<211> LENGTH: 32
<212> TYPE: DNA
<213> ORGANISM: Homo sapiens

<400> SEQUENCE: 115
catacccgct ttcaatacac aaaggtgatc tg                               32

<210> SEQ ID NO 116
<211> LENGTH: 30
<212> TYPE: DNA
<213> ORGANISM: Homo sapiens

<400> SEQUENCE: 116
cttccacagg atctgtgaac tctttcggtc                                  30

<210> SEQ ID NO 117
<211> LENGTH: 29
<212> TYPE: DNA
<213> ORGANISM: Homo sapiens

<400> SEQUENCE: 117
ctgcctaaga gttagccctg ctctggaag                                   29

<210> SEQ ID NO 118
<211> LENGTH: 29
<212> TYPE: DNA
<213> ORGANISM: Homo sapiens

<400> SEQUENCE: 118
tggacccgct tttctcaaag tgtggtccg                                   29

<210> SEQ ID NO 119
<211> LENGTH: 28
```

<212> TYPE: DNA
<213> ORGANISM: Homo sapiens

<400> SEQUENCE: 119
cagagcctct tgtagataag tgggtcag                              28

<210> SEQ ID NO 120
<211> LENGTH: 25
<212> TYPE: DNA
<213> ORGANISM: Homo sapiens

<400> SEQUENCE: 120
ttaccacaga gaaaaagcag gaccc                                 25

<210> SEQ ID NO 121
<211> LENGTH: 29
<212> TYPE: DNA
<213> ORGANISM: Homo sapiens

<400> SEQUENCE: 121
gttccagaca gtggaatgat ggggctcag                             29

<210> SEQ ID NO 122
<211> LENGTH: 30
<212> TYPE: DNA
<213> ORGANISM: Homo sapiens

<400> SEQUENCE: 122
cagacccaga gtttgcacgc tatgtggcag                            30

<210> SEQ ID NO 123
<211> LENGTH: 24
<212> TYPE: DNA
<213> ORGANISM: Homo sapiens

<400> SEQUENCE: 123
cagagcccct gcactcagag gcag                                  24

<210> SEQ ID NO 124
<211> LENGTH: 25
<212> TYPE: DNA
<213> ORGANISM: Homo sapiens

<400> SEQUENCE: 124
cttccaccgt gggaccctct gcagg                                 25

<210> SEQ ID NO 125
<211> LENGTH: 29
<212> TYPE: DNA
<213> ORGANISM: Homo sapiens

<400> SEQUENCE: 125
tgtggcctct tttaggtgaa gctgctcca                             29

<210> SEQ ID NO 126
<211> LENGTH: 29
<212> TYPE: DNA
<213> ORGANISM: Homo sapiens

<400> SEQUENCE: 126
cagagcctcc tggccatctc ctgtggaag                             29

<210> SEQ ID NO 127

```
<210> SEQ ID NO 127
<211> LENGTH: 30
<212> TYPE: DNA
<213> ORGANISM: Homo sapiens

<400> SEQUENCE: 127
cgtatccact tccttatccc ttggtggaag                                    30

<210> SEQ ID NO 128
<211> LENGTH: 27
<212> TYPE: DNA
<213> ORGANISM: Homo sapiens

<400> SEQUENCE: 128
cggtgccgag actcccaagc ggctctg                                       27

<210> SEQ ID NO 129
<211> LENGTH: 24
<212> TYPE: DNA
<213> ORGANISM: Homo sapiens

<400> SEQUENCE: 129
ctatcacaca ctgctttgtg taag                                          24

<210> SEQ ID NO 130
<211> LENGTH: 28
<212> TYPE: DNA
<213> ORGANISM: Homo sapiens

<400> SEQUENCE: 130
gagcgcccca gtcactgctc tgtggaag                                      28

<210> SEQ ID NO 131
<211> LENGTH: 29
<212> TYPE: DNA
<213> ORGANISM: Homo sapiens

<400> SEQUENCE: 131
cttccccagt ttaaaatcaa tccactccg                                     29

<210> SEQ ID NO 132
<211> LENGTH: 30
<212> TYPE: DNA
<213> ORGANISM: Homo sapiens

<400> SEQUENCE: 132
cgtacccgct caccttgggc tctggggcag                                    30

<210> SEQ ID NO 133
<211> LENGTH: 29
<212> TYPE: DNA
<213> ORGANISM: Homo sapiens

<400> SEQUENCE: 133
ctgagcatct ttgaactaat tcagctctg                                     29

<210> SEQ ID NO 134
<211> LENGTH: 34
<212> TYPE: DNA
<213> ORGANISM: Homo sapiens

<400> SEQUENCE: 134
cagacccggt tacctggggt tcaatctctg ggag                               34
```

<210> SEQ ID NO 135
<211> LENGTH: 29
<212> TYPE: DNA
<213> ORGANISM: Homo sapiens

<400> SEQUENCE: 135
ctgccccaga gcttccaact ctgggaatc                              29

<210> SEQ ID NO 136
<211> LENGTH: 30
<212> TYPE: DNA
<213> ORGANISM: Homo sapiens

<400> SEQUENCE: 136
atctgccaga gttatgttaa agggctctg                              30

<210> SEQ ID NO 137
<211> LENGTH: 32
<212> TYPE: DNA
<213> ORGANISM: Homo sapiens

<400> SEQUENCE: 137
agggtcccct ctcccacggc cctctgggga ag                          32

<210> SEQ ID NO 138
<211> LENGTH: 29
<212> TYPE: DNA
<213> ORGANISM: Homo sapiens

<400> SEQUENCE: 138
caaagccttg tccaaatact ctgtggcag                              29

<210> SEQ ID NO 139
<211> LENGTH: 29
<212> TYPE: DNA
<213> ORGANISM: Homo sapiens

<400> SEQUENCE: 139
ctgcccttga gttttataaa ggggctatg                              29

<210> SEQ ID NO 140
<211> LENGTH: 29
<212> TYPE: DNA
<213> ORGANISM: Homo sapiens

<400> SEQUENCE: 140
gtcatcctca tctcacggat gaggatgcc                              29

<210> SEQ ID NO 141
<211> LENGTH: 29
<212> TYPE: DNA
<213> ORGANISM: Homo sapiens

<400> SEQUENCE: 141
gtcgtcctca tcttaataaa ctgcaaaaa                              29

<210> SEQ ID NO 142
<211> LENGTH: 30
<212> TYPE: DNA
<213> ORGANISM: Homo sapiens

<400> SEQUENCE: 142
gtcatcctca tcttcatcca tgaggaagag                             30

```
<210> SEQ ID NO 143
<211> LENGTH: 29
<212> TYPE: DNA
<213> ORGANISM: Homo sapiens

<400> SEQUENCE: 143
ctctttcagt taagtaggga ctggaaaag                                          29

<210> SEQ ID NO 144
<211> LENGTH: 29
<212> TYPE: DNA
<213> ORGANISM: Homo sapiens

<400> SEQUENCE: 144
cttgtgttgt gtgtattcaa ctcacagag                                          29

<210> SEQ ID NO 145
<211> LENGTH: 29
<212> TYPE: DNA
<213> ORGANISM: Homo sapiens

<400> SEQUENCE: 145
cttccatata gttagagact ctgtggcag                                          29
```